US010155071B2

(12) United States Patent
Locke et al.

(10) Patent No.: US 10,155,071 B2
(45) Date of Patent: Dec. 18, 2018

(54) REDUCED-PRESSURE SYSTEMS, METHODS, AND DEVICES FOR SIMULTANEOUSLY TREATING A PLURALITY OF TISSUE SITES

(71) Applicant: KCI Licensing, Inc., San Antonio, TX (US)

(72) Inventors: Christopher Brian Locke, Bournemouth (GB); Richard Daniel John Coulthard, Verwood (GB); James Luckemeyer, San Antonio, TX (US); Richard Marvin Kazala, Jr., San Antonio, TX (US); Benjamin A. Pratt, Poole (GB); Timothy Mark Robinson, Basingstoke (GB)

(73) Assignee: KCI Licensing, Inc., San Antonio, TX (US)

( * ) Notice: Subject to any disclaimer, the term of this patent is extended or adjusted under 35 U.S.C. 154(b) by 541 days.

(21) Appl. No.: 13/681,731

(22) Filed: Nov. 20, 2012

(65) Prior Publication Data
US 2013/0144227 A1    Jun. 6, 2013

Related U.S. Application Data

(60) Provisional application No. 61/563,284, filed on Nov. 23, 2011.

(51) Int. Cl.
*A61M 1/00* (2006.01)
*A61M 27/00* (2006.01)
*A61F 13/00* (2006.01)

(52) U.S. Cl.
CPC ........ *A61M 1/0031* (2013.01); *A61M 1/0015* (2014.02); *A61M 1/0035* (2014.02);
(Continued)

(58) Field of Classification Search
CPC .............. A61M 1/0009; A61M 1/0031; A61M 1/0088; A61M 2205/21; A61M 2205/84;
(Continued)

(56) References Cited

U.S. PATENT DOCUMENTS 1,355,846 A    10/1920   Rannells
2,547,758 A     4/1951   Keeling
(Continued)

FOREIGN PATENT DOCUMENTS

AU    550575 A1    8/1982
AU    745271       4/1999
(Continued)

OTHER PUBLICATIONS

International Search Report and Written Opinion for corresponding PCT/US2012/066081, dated Feb. 15, 2013.
(Continued)

*Primary Examiner* — Andrew J Mensh

(57) ABSTRACT

Systems and methods for treating a plurality of tissue sites include a multi-port therapy unit. The multi-port therapy unit includes a plurality of patient-side ports each fluidly coupled to a plurality of conduits and a fluid reservoir fluidly coupled to the plurality of ports. A plurality of pressure sensors are associated with the plurality of patient-side ports to determining a pressure associated with each conduit. A controller is operatively coupled to the plurality of pressure sensors to receive treatment pressure data, monitor pressure for each pressure sensor of the plurality of pressure sensors, and signal an alarm condition if the pressure is outside of a pre-selected range. The system includes a reduced-pressure source fluidly coupled to a dressing at each tissue site through the multi-port therapy unit.

10 Claims, 13 Drawing Sheets

(52) U.S. Cl.
CPC . *A61F 13/00068* (2013.01); *A61F 2013/0054* (2013.01); *A61F 2013/00536* (2013.01); *A61M 1/0009* (2013.01); *A61M 1/0023* (2013.01); *A61M 1/0025* (2014.02); *A61M 1/0027* (2014.02); *A61M 1/0088* (2013.01); *A61M 27/00* (2013.01); *A61M 2205/15* (2013.01); *A61M 2205/18* (2013.01); *A61M 2205/21* (2013.01); *A61M 2205/3344* (2013.01); *A61M 2205/584* (2013.01); *A61M 2205/84* (2013.01)

(58) Field of Classification Search
CPC ............ A61M 2205/15; A61M 1/0015; A61M 1/0035; A61M 1/0027; A61M 2205/18; A61M 2205/3344; A61M 2205/584; A61M 1/0023; A61M 27/00; A61M 1/0025; A61F 2013/00536; A61F 13/00068; A61F 2013/0054
USPC ...................................................... 604/318
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A * | 11/1993 | Zamierowski | 604/180 |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2002/0198504 A1 * | 12/2002 | Risk, Jr. | A61M 1/0058 604/318 |
| 2006/0025727 A1 * | 2/2006 | Boehringer | A61M 1/0011 604/313 |
| 2009/0281509 A1 | 11/2009 | Gellis | |
| 2011/0071484 A1 | 3/2011 | Song | |
| 2011/0130712 A1 * | 6/2011 | Topaz | 604/23 |
| 2011/0178481 A1 * | 7/2011 | Locke et al. | 604/319 |

(56) References Cited

U.S. PATENT DOCUMENTS

| | | |
|---|---|---|
| 2014/0163491 A1 | 6/2014 | Schuessler et al. |
| 2015/0080788 A1 | 3/2015 | Blott et al. |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| DE | 102006051223 A1 | 11/2007 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/010424 | 9/1990 |
| WO | WO 93/009727 | 5/1993 |
| WO | WO 94/020041 | 9/1994 |
| WO | WO 96/05873 | 2/1996 |
| WO | WO 97/18007 | 5/1997 |
| WO | WO 99/13793 | 3/1999 |
| WO | WO 2008/027449 A2 | 3/2008 |
| WO | WO 2008/098207 A2 | 8/2008 |
| WO | WO 2009/141820 A1 | 11/2009 |
| WO | 2012067916 A1 | 5/2012 |

OTHER PUBLICATIONS

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96 (certified translation).

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & dated Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, YU. A., et al; "Vacuum Therapy in the Treatment of Purulent Lactation Mastitis"; Vestnik Khirurgi, May 14, 1986, pp. 66-70, and 9 page English translation thereof.

Yusupov. YU. N., et al; "Active Wound Drainage", Vestnik Khirurgi, vol. 138, Issue 4, 1987, and 7 page English translation thereof.

Davydov, YU. A., et al; "Bacteriological and Cytological Assessment of Vacuum Therapy for Purulent Wounds"; Vestnik Khirurgi, Oct. 1988, pp. 48-52, and 8 page English translation thereof.

Davydov, YU. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.

G. Živadinović, V. Ðukić, Ž. Maksimović, Ð. Radak, and P. Peška, "Vacuum Therapy in the Treatment of Peripheral Blood Vessels," *Timok Medical Journal* 11 (1986), pp. 161-164 (certified translation).

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

(56) References Cited

OTHER PUBLICATIONS

C.E. Tennants, "The Use of Hypermia in the Postoperative Treatment of Lesions of the Extremities and Thorax," *Journal of the American Medical Association* 64 (1915), pp. 1548-1549.
Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).
European Search Report for EP 12795284.4 dated Apr. 9, 2015.
European Examination Report for corresponding Application No. 161897293, dated Apr. 26, 2018.

* cited by examiner

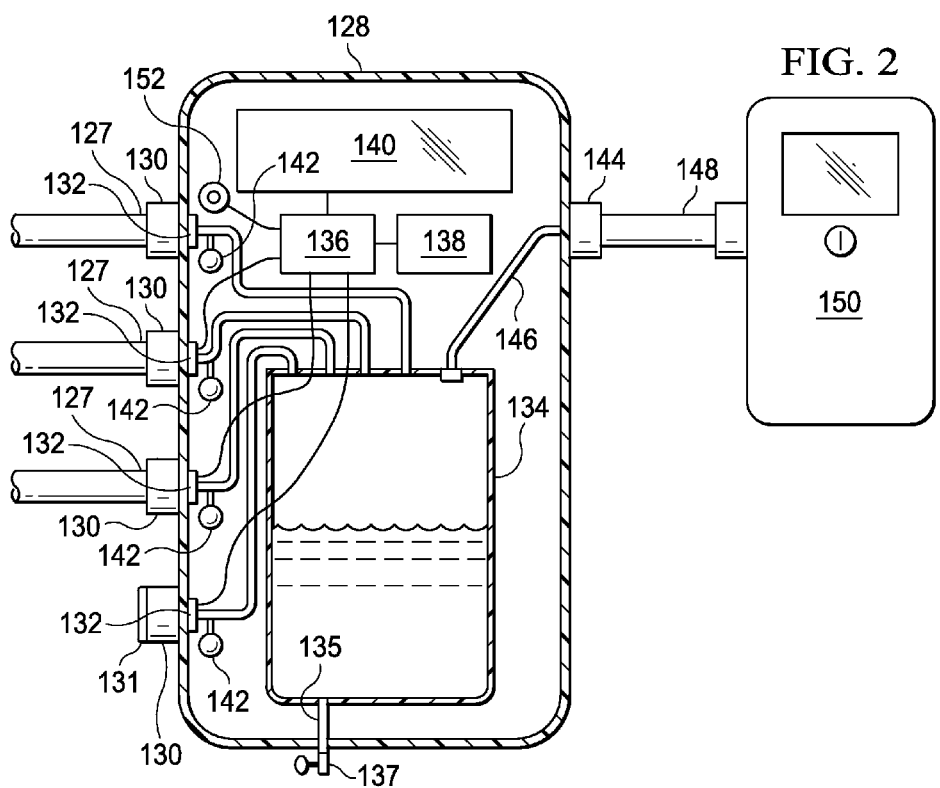
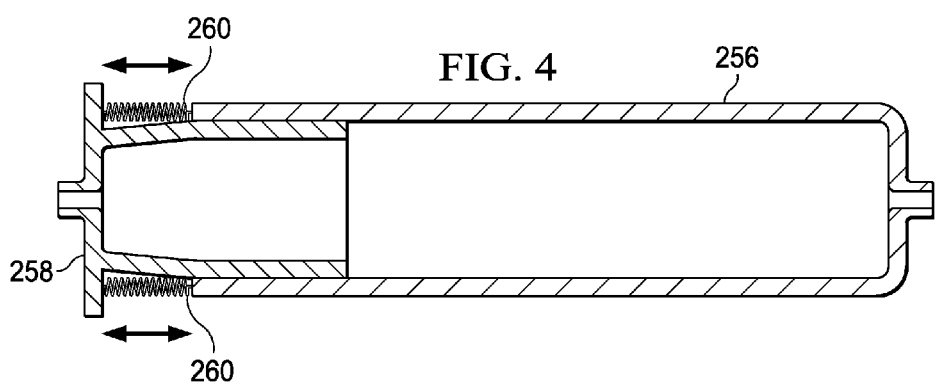

LEAK DETERMINATION USING PRESSURE RAMP UP

REDUCED-PRESSURE SYSTEMS, METHODS, AND DEVICES FOR SIMULTANEOUSLY TREATING A PLURALITY OF TISSUE SITES

CROSS-REFERENCE TO RELATED APPLICATION

This application claims priority to U.S. Provisional Patent Application No. 61/563,284 filed Nov. 23, 2011, entitled REDUCED-PRESSURE SYSTEMS, METHODS, AND DEVICES FOR SIMULTANEOUSLY TREATING A PLURALITY OF TISSUE SITES, the disclosure of which is hereby incorporated by reference in its entirety.

BACKGROUND OF THE INVENTION

1. Field of the Invention

The present disclosure relates generally to medical systems, devices, and methods for treating a patient with reduced pressure, and more particularly, but not by way of limitation, to medical systems, devices, and methods for simultaneously treating a plurality of tissue sites.

2. Description of Related Art

Clinical studies and practice have shown that providing reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. At times, it may be necessary to treat a plurality of tissue sites. This is particularly true of patients injured by burns, war, or other trauma. Moreover, the plurality of tissue sites may need to be treated in the field or during transportation.

SUMMARY

Systems, methods, and devices are presented that facilitate the simultaneous treatment of a plurality of tissue sites with reduced pressure.

In an illustrative embodiment, a system for simultaneously treating a plurality of tissue sites on a patient is disclosed. The system includes a plurality of reduced-pressure dressings, and a plurality of multi-lumen reduced-pressure delivery conduits. Each multi-lumen reduced-pressure delivery conduit includes at least one pressure-sampling lumen and at least one reduced-pressure supply lumen. The system also includes a multi-port therapy unit. The multi-port therapy unit includes a plurality of patient-side ports. Each of the plurality of patient-side ports is configured to fluidly couple with one of the plurality of multi-lumen reduced-pressure delivery conduits and with at least one of the pressure-sampling lumens and one of the reduced-pressure supply lumens therein. The multi-port therapy unit also includes a fluid reservoir fluidly coupled to the plurality of patient-side ports, and a plurality of pressure sensors. The plurality of pressure sensors are associated with the plurality of patient-side ports for determining a pressure associated with each of the plurality of pressure-sampling lumens. The multi-port therapy unit further includes a controller operatively coupled to the plurality of pressure sensors for receiving treatment pressure data from the plurality of pressure sensors. The controller includes a microprocessor and memory configured to monitor pressure for each of the plurality of pressure sensors and to signal an alarm condition if the pressure is outside of a pre-selected range. The multi-port therapy unit also includes an electrical source operatively coupled to the controller, and a supply-side port for receiving reduced pressure. The supply-side port is fluidly coupled to the fluid reservoir. The multi-port therapy unit also includes an alarm indicator operatively coupled to the controller for indicating when the controller signals an alarm condition. The system further includes a reduced-pressure source fluidly coupled to the supply-side port.

In another illustrative embodiment, a method for treating a plurality of tissue sites on a patient is disclosed. The method deploys a plurality of reduced-pressure dressings proximate to the plurality of tissue sites and fluidly couples the plurality of reduced-pressure dressings to a multi-port therapy unit. The multi-port therapy unit includes a plurality of patient-side ports. Each of the plurality of patient-side ports is configured to fluidly couple with one of the plurality of multi-lumen reduced-pressure delivery conduits and with at least one of the pressure-sampling lumens and one of the reduced-pressure supply lumens therein. The multi port therapy unit further includes a fluid reservoir fluidly coupled to the plurality of patient-side ports and a plurality of pressure sensors. The plurality of pressure sensors are associated with the plurality of patient-side ports for determining a pressure associated with each of the plurality of pressure-sampling lumens. The multi-port therapy unit further includes a controller operatively coupled to the plurality of pressure sensors for receiving treatment pressure data from the plurality of pressure sensors. The controller includes a microprocessor and memory configured to monitor pressure for, each of the plurality of pressure sensors and to signal an alarm condition if the pressure is outside of a pre-selected range. An electrical source is operatively coupled to the controller. The multi-port therapy unit further includes a supply-side port for receiving reduced pressure. The supply-side port is fluidly coupled to the fluid reservoir, and an alarm indicator is operatively coupled to the controller for indicating when the controller signals an alarm condition. The method activates the multi-port therapy unit to deliver reduced pressure simultaneously to the plurality of reduced-pressure dressings and to monitor pressure for each of the plurality of reduced-pressure dressings.

In still another illustrative embodiment, a system for simultaneously treating a plurality of tissue sites on a patient is disclosed. The system includes a plurality of reduced pressure dressings and a plurality of multi-lumen reduced-pressure delivery conduits. Each multi-lumen reduced-pressure delivery conduit includes at least a pressure-sampling lumen and at least a reduced-pressure supply lumen. The system further includes a fluid storage device fluidly coupled to the plurality of reduced-pressure dressings for receiving and at least temporarily storing fluids, and a multi-port therapy unit. The multi-port therapy unit includes a controller and a plurality of patient-side ports. Each of the plurality of patient-side ports is configured to fluidly couple with one of the plurality of multi-lumen reduced-pressure delivery conduits and with at least one of the pressure-sampling lumens and one of the reduced-pressure supply lumens therein. The multi-port therapy unit also includes a plurality of reduced-pressure plenums, each of the plurality of reduced-pressure plenums associated with one of the plurality of patient-side ports. The multi-port therapy unit further includes a plurality of treatment pressure sensors. Each of the plurality of treatment pressure sensors is associated with one of the plurality of patient-side ports for determining a pressure associated with the at least one pressure-sampling lumen in the multi-lumen reduced-pressure delivery conduit associated with the patient-side port. Each treatment pressure sensor is operatively coupled to the controller to provide a treatment pressure signal to the controller. The multi-port therapy unit also includes a plurality of plenum pressure sensors. Each of the plurality of plenum pressure sensors is associated with one of the plurality of reduced-pressure plenums and is operatively coupled to the controller for supplying a plenum pressure signal. The multi-port therapy unit further includes a first plurality of control valves fluidly coupled between each of the plurality of reduced-pressure plenums and an associated patient-side port. Each of the first plurality of control valves is operatively coupled to the controller so that each of the first plurality of control valves may be controlled by the controller. The multi-port therapy unit also includes a main vacuum source fluidly coupled to each of the plurality of plenums for supplying reduced pressure to each of the plurality of reduced-pressure plenums, and a second plurality of control valves fluidly coupled between each of the plurality of reduced-pressure plenums and the main vacuum source. The controller is operative to regulate the reduced pressure supplied from the plurality of reduced-pressure plenums to the plurality of patient-side ports by controlling the first plurality of control valves and to regulate the reduced pressure supplied to the plurality of reduced-pressure plenums using the second plurality of control valves.

In yet another illustrative embodiment, a system for simultaneously treating a plurality of tissue sites on a patient is disclosed. The system includes a plurality of reduced-pressure dressings and a plurality of multi-lumen reduced-pressure delivery conduits. Each multi-lumen reduced-pressure delivery conduit includes at least a pressure-sampling lumen and at least a reduced-pressure supply lumen. The system also includes a fluid storage device fluidly coupled to the plurality of reduced-pressure dressings for receiving fluids therefrom and a multi-port therapy unit. The multi-port therapy unit includes a plurality of pressure ports. Each of the plurality of pressure ports is configured to fluidly couple with at least one of the pressure-sampling lumens of the plurality of multi-lumen reduced-pressure delivery conduits. The multi-port therapy unit also includes a treatment pressure sensor fluidly coupled to the plurality of pressure sampling lumens associated with the plurality of multi-lumen reduced-pressure delivery conduits by a plurality of delivery conduits. The multi-port therapy unit further includes a valve means fluidly coupled to the treatment pressure sensor and the plurality of pressure ports for selectively controlling the flow from each of the plurality of pressure ports to the treatment pressure sensor. In addition, the multi-port therapy unit includes a reduced-pressure source fluidly coupled to the plurality of reduced-pressure dressings, and a controller operatively coupled to the treatment pressure sensor, the plurality of valves, and the reduced-pressure source. The controller is configured to monitor the reduced pressure of each of the plurality of pressure-sampling lumens associated with the plurality of multi-lumen reduced-pressure delivery conduits and in response to control the reduced pressure delivered by the reduced-pressure source.

In still another illustrative embodiment, a system for simultaneously treating a plurality of tissue sites on a patient is disclosed. The system includes a plurality of reduced-pressure dressings and a plurality of multi-lumen reduced-pressure delivery conduits. Each multi-lumen reduced-pressure delivery conduit includes at least a pressure-sampling lumen and reduced-pressure supply lumen. The system also includes a fluid storage device fluidly coupled to the plurality of reduced-pressure dressings for receiving fluids therefrom and a multi-port therapy unit. The multi-port therapy unit includes a controller and a plurality of pressure ports. Each of the plurality of pressure ports is configured to fluidly couple with at least one of the pressure-sampling lumens of the plurality of multi-lumen reduced-pressure delivery conduits. The multi-port therapy unit further includes a plurality of treatment pressure sensors fluidly coupled to the plurality of pressure ports and operatively coupled to the controller, and a reduced-pressure source fluidly coupled to the plurality of reduced-pressure dressings. The controller is operatively coupled to the plurality of treatment pressure sensors and the reduced-pressure source. The controller is configured to monitor the reduced pressure of each of the plurality of pressure-sampling lumens associated with the plurality of multi-lumen reduced-pressure delivery conduits and to control the reduced pressure delivered by the reduced-pressure source.

Aspects, features, and advantages of the illustrative embodiments will become apparent with reference to the drawings and detailed description that follow.

BRIEF DESCRIPTION OF THE DRAWINGS

FIG. 2 is an elevation view of an illustrative embodiment of a multi-port therapy unit and an illustrative reduced-pressure source from FIG. 1;

FIG. 4 is a cross-sectional view of an illustrative embodiment of a reduced-pressure plenum for use as an aspect of the system of FIG. 3;

DETAILED DESCRIPTION OF ILLUSTRATIVE EMBODIMENTS

In the following detailed description of illustrative, non-limiting embodiments, reference is made to the accompanying drawings that form a part hereof. These embodiments are described in sufficient detail to enable those skilled in the art to practice the invention, and it is understood that other embodiments may be utilized and that logical, structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is not to be taken in a limiting sense, and the scope of the illustrative embodiments is defined only by the appended claims.

Figure 1:
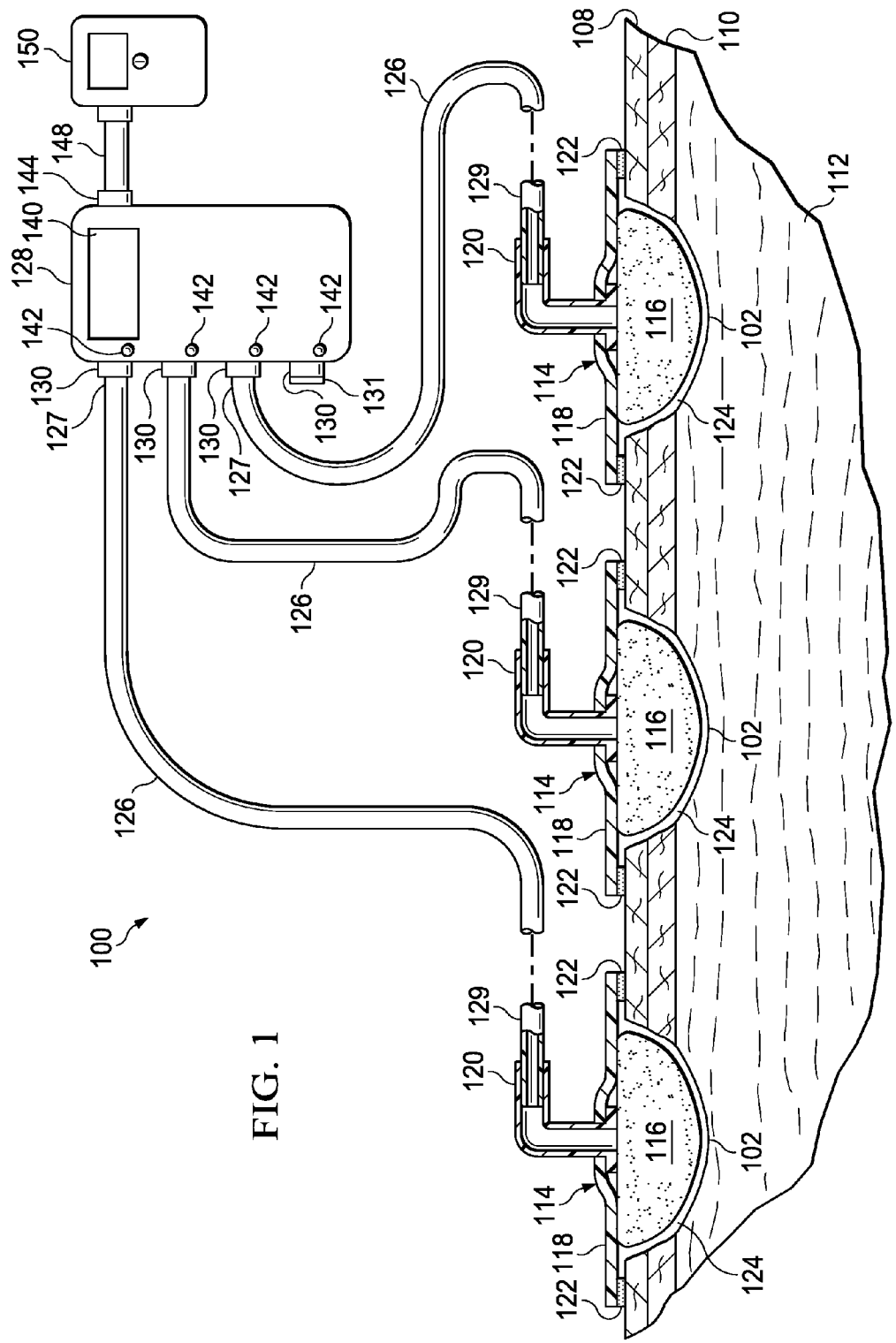
FIG. 1 is a cross-sectional view (with a portion shown in elevation view) of an illustrative embodiment of a system for simultaneously treating a plurality of tissue sites on a patient.

Referring now to the figures and primarily to FIGS. 1-2, an illustrative embodiment of a system 100 for simultaneously treating a plurality of tissue sites 102 is presented. Each tissue site 102 may be the bodily tissue of any human, animal, or other organism, including bone tissue, adipose tissue, muscle tissue, dermal tissue, vascular tissue, connective tissue, cartilage, tendons, ligaments, or any other tissue. Treatment of tissue sites 102 may include removal of fluids, e.g., exudate or ascites. While numerous tissue sites, sizes, and depths may be treated with the system 100, the system 100 is shown treating tissue sites 102 in the form of wounds. The wounds are shown for illustrative purposes extending through epidermis 108, dermis 110, and into subcutaneous tissue 112. Other depths or types of wounds or, more generally, tissue sites may be treated. While three tissue sites 102 are shown for illustration purposes, it should be understood that any number of tissue sites—typically two or greater—may be treated with the system 100.

The system 100 includes a plurality of reduced-pressure dressings 114 deployed on the plurality of tissue sites 102. Each of the plurality of reduced-pressure dressings 114 may be any kind of dressing that allows reduced pressure to be delivered to the tissue site 102 associated with the reduced-pressure dressing 114 and that is operable to remove fluids from the tissue site 102. In one illustrative embodiment, each reduced-pressure dressing 114 includes a manifold 116, a sealing member 118, and a reduced-pressure interface 120. The sealing member 118 is releasably coupled to the tissue site 102 using an attachment device 122. The attachment device 122 may take numerous forms. For example, the attachment device 122 may be a medically acceptable, pressure-sensitive adhesive that extends about a periphery, a portion, or the entire sealing member 118; a double-sided drape tape; paste; hydrocolloid; hydro-gel; silicone gel, oraganogel, or other sealing devices or elements. For each reduced-pressure dressing 114, the sealing member 118 creates a sealed space 124 containing the manifold 116 and the tissue site 102 to be treated.

For each reduced-pressure dressing 114, the manifold 116 is a substance or structure that is provided to assist in applying reduced pressure to, delivering fluids to, or removing fluids from the associated tissue site 102. The manifold 116 includes a plurality of flow channels or pathways that distribute fluids provided to and removed from the tissue site 102 around the manifold 116. In one illustrative embodiment, the flow channels or pathways are interconnected to improve distribution of fluids provided to or removed from the tissue site 102. The manifold 116 may comprise, for example, one or more of the following: a biocompatible material that is capable of being placed in contact with the tissue site 102 and distributing reduced pressure to the tissue site 102; devices that have structural elements arranged to form flow channels, such as, for example, cellular foam, open-cell foam, porous tissue collections, liquids, gels, and foams that include, or cure to include, flow channels; porous materials, such as foam, gauze, felted mat, or any other material suited to a particular biological application; or porous foam that includes a plurality of interconnected cells or pores that act as flow channels, e.g., a polyurethane, open-cell, reticulated foam such as GranuFoam® material manufactured by Kinetic Concepts, Incorporated of San Antonio, Tex.; a bioresorbable material; or a scaffold material. In some situations, the manifold 116 may also be used to distribute fluids such as medications, antibacterials, growth factors, and various solutions to the tissue site 102. Other layers may be included in or on the manifold 116, such as absorptive materials, wicking materials, hydrophobic materials, and hydrophilic materials.

In one illustrative, non-limiting embodiment, the manifold 116 may be constructed from a bioresorbable material that can remain in a patient's body following use of the reduced-pressure dressing 114. Suitable bioresorbable materials may include, without limitation, a polymeric blend of polylactic acid (PLA) and polyglycolic acid (PGA). The polymeric blend may also include without limitation polycarbonates, polyfumarates, and capralactones. The manifold 116 may further serve as a scaffold for new cell-growth, or a scaffold material may be used in conjunction with the manifold 116 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The sealing member 118 may be any material that provides a fluid seal. A fluid seal is a seal adequate to maintain reduced pressure at a desired site given the particular reduced-pressure source or subsystem involved. The sealing member 118 may be, for example, an impermeable or semi-permeable, elastomeric material. For semi-permeable materials, the permeability must be low enough that for a given reduced-pressure source, the desired reduced pressure may be maintained. The sealing member 118 may be discrete pieces for each reduced-pressure dressing 114 or may be one continuous sheet used for all the plurality of reduced-pressure dressings 114.

Each of the plurality of reduced-pressure interfaces 120 is fluidly coupled to the associated sealed space 124 for the tissue site 102. The reduced-pressure interfaces 120 may each be any device for delivering reduced pressure to the associated sealed space 124. For example, each of the reduced-pressure interfaces 120 may comprise one of the following: a T.R.A.C.® Pad or Sensa T.R.A.C.® Pad available from KCI of San Antonio, Tex.; or another device or tubing. A plurality of multi-lumen reduced-pressure delivery conduits 126 are fluidly coupled to the plurality of reduced-pressure interfaces 120 in a one-to-one fashion. Each of the plurality of multi-lumen reduced-pressure delivery conduits 126 has a first end 127 and a second end 129. Each first end 127 of the multi-lumen reduced-pressure delivery conduits 126 is fluidly coupled to a multi-port therapy unit 128. Each of the plurality of multi-lumen reduced-pressure delivery conduits 126 may include at least one pressure-sampling lumen and at least one reduced-pressure supply lumen. The pressure-sampling lumen provides a pressure for determining the pressure or approximate pressure at the associated reduced-pressure dressing 114. The reduced-pressure supply lumen delivers the reduced pressure to the reduced-pressure dressing 114 and receives fluids therefrom. The second end 129 of each multi-lumen reduced-pressure delivery conduit 126 is fluidly coupled to a respective reduced-pressure interface 120.

The multi-port therapy unit 128 provides reduced pressure through the multi-lumen reduced-pressure delivery conduits 126 and reduced-pressure interfaces 120 to the sealed spaces 124. In addition, the multi-port therapy unit 128 receives pressure from the at least one pressure-sampling lumen of each of the plurality of multi-lumen reduced-pressure delivery conduits 126 and determines the pressure thereof.

Reduced pressure includes a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Unless otherwise indicated, quantitative values of pressure stated herein are gauge pressures. The reduced pressure delivered may be constant or varied (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, unless otherwise indicated, an increase in reduced pressure or vacuum pressure typically refers to a reduction in absolute pressure.

The multi-port therapy unit 128 includes a plurality of patient-side ports 130. Each of the plurality of patient-side ports 130 is configured to fluidly couple to one of the multi-lumen reduced-pressure delivery conduits 126 and in particular with at least one of the pressure-sampling lumens and one of the reduced-pressure supply lumens of the plurality of multi-lumen reduced-pressure delivery conduits 126. Patient-side ports 130 not in use may be sealed by a cap 131.

A fluid reservoir 134 is fluidly coupled to the plurality of patient-side ports 130 to provide reduced pressure thereto and receive fluids therefrom. A drain conduit 135 may fluidly couple the fluid reservoir 134 to an exterior for draining the fluid reservoir 134. A valve 137 associated with the drain conduit 135 selectively controls fluid exiting the drain conduit 135. The valve 137 may be manual or may be automated and coupled to a controller 136. Unless otherwise indicated, as used throughout this document, "or" does not require mutual exclusivity.

The multi-port therapy unit 128 also includes a plurality of pressure sensors 132, or pressure transducers, that provide a treatment pressure signal to the controller 136. The controller 136 may be a printed wire assembly (PWA) or an application specific integrated circuit (ASIC) with a microprocessor and memory or other control device. The plurality of pressure sensors 132 are associated with the plurality of patient-side ports 130 for determining a pressure associated with each of the plurality of patient-side ports 130 and typically with the pressure-sampling lumen therein that carries the approximate pressure at the reduced-pressure dressing 114. Pressure associated with each of the plurality of patient-side ports 130 may include the pressure at the port itself or proximate the port in an internal conduit. In any event, each pressure sensor 132 measures pressure a respective pressure-sampling lumen.

The controller 136 is operatively coupled to the plurality of pressure sensors 132 for receiving treatment pressure data from the plurality of pressure sensors 132. The controller 136 includes a microprocessor and memory configured to monitor pressure for each of the plurality of pressure sensors 132 and to signal an alarm condition if the pressure leaves a desired range or goes below a minimum reduced pressure threshold (i.e., the absolute pressure rises above a threshold). The controller 136 is electrically coupled to an electrical power source 138, which may be a battery or fixed power line, for example. A user interface 140 is operatively coupled to the controller 136 for providing information readouts or for receiving user inputs.

The multi-port therapy unit 128 may include a plurality of visual indicators 142. The visual indicators 142 visually alert users when a pressure below a first threshold exists (i.e., above an absolute pressure threshold) at one of the plurality of patient-side ports 130.

The multi-port therapy unit 128 also includes a supply-side port 144 for receiving reduced pressure. The supply-side port 144 is fluidly coupled to the fluid reservoir 134 such as by an internal conduit 146. The supply-side port 144 is also fluidly coupled by a conduit 148 to a reduced-pressure source 150.

The reduced-pressure source 150 may be any device for supplying a reduced pressure, such as a vacuum pump, wall suction, or other source. While the amount and nature of reduced pressure applied to a tissue site will typically vary according to the application, the reduced pressure will typically be between −5 mm Hg (−667 Pa) and −500 mm Hg (−66.7 kPa) and more typically between −75 mm Hg (−9.9 kPa) and −300 mm Hg (−39.9 kPa). In some embodiments, the reduced-pressure source 150 may be a V.A.C. Freedom, V.A.C. ATS, InfoVAC, ActiVAC, ABThera, or V.A.C. Ulta therapy units available from KCI of San Antonio, Tex.

In operation according to one illustrative embodiment, the reduced-pressure source 150 is fluidly coupled to the supply-side port 144 of the multi-port therapy unit 128. The caps 131, or sealing caps, are removed from the plurality of patient-side ports 130 in a number corresponding to the number of tissue sites 102 that are to be treated. The first ends 127 of the plurality of multi-lumen reduced-pressure delivery conduits 126 are coupled to the uncapped members of the plurality of patient-side ports 130. The plurality of reduced-pressure dressings 114 are deployed on the plurality of tissue sites 102. The second ends 129 of the plurality of multi-lumen reduced-pressure delivery conduits 126 are fluidly coupled to the plurality of reduced-pressure dressings 114. The reduced-pressure source 150 is activated to supply reduced pressure to the fluid reservoir 134 and to the tissue sites 102. As liquids are removed from the tissue sites 102, the liquids begin to fill the fluid reservoir 134. Optionally, after fluid reservoir 134 is full, the fluid may continue into a fluid reservoir contained within the reduced-pressure source 150. Alternatively, a hydrophobic or oleophobic filter may be included as part of the supply-side port 144 to prevent liquids from reaching the reduced-pressure source 150.

The multi-port therapy unit 128 monitors pressure at the tissue sites 102 for each of the connected reduced-pressure dressings 114. Each pressure sensor 132 develops a treatment pressure signal that is delivered to the controller 136 for monitoring. The microprocessor and memory or other aspects of controller 136 are used to monitor the treatment pressure signals to confirm compliance with the desired pressure range. The pressure in each tissue site 102 may be displayed on the user interface 140 constantly or with a cycled pattern. Alternatively or in addition, separate multi-colored LED indicators may be included to provide a quick color indication of pressure and status at each of the plurality of patient-side ports 130. For example, the multi-colored LED indicators may be able to assume the colors green, yellow, and red. The controller 136 may be programmed to produce a green light when the pressure is between −75 mm Hg and −150 mm Hg. A yellow light may be signaled if the wound pressure declines (i.e., loses reduced pressure so that pressure is greater on an absolute pressure scale) indicating a dressing leak. A red light may be used to indicate the wound pressure is below a reduced pressure threshold (e.g., −40 mm Hg) and is not providing adequate therapy. A flashing red light may mean that an over pressure (e.g., more negative than −200 mm Hg) has been applied. In this regard, a relief valve may also be included. Under this illustrative example, if a yellow or red light is given, the caregiver may find and address a leak that is in the associated reduced-pressure dressing 114, disconnect the multi-lumen reduced-pressure delivery conduit 126 associated with that particular reduced-pressure dressing 114 and reattach the cap 131 to avoid compromising the reduced pressure available for other tissue sites 102. In addition, the caregiver may connect a separate therapy unit (reduced pressure source and fluid reservoir) to the apparently leaking reduced-pressure dressing 114 so that reduced pressure may continue to be supplied until a more convenient time is available for addressing the situation.

The controller 136 may also optionally activate an audible alarm 152, but given tight quarters for many transportation operations, this feature may be turned off or not included. Typically, if it is a desire to purge the plurality of multi-lumen reduced-pressure delivery conduits 126, they will be purged together. If the red light is indicated, the caregiver checks the multi-lumen reduced-pressure delivery conduits 126 for blockage and replaces any blocked conduits if necessary.

In one illustrative embodiment, the fluid reservoir 134 in the multi-port therapy unit 128 is an off-the-shelf canister. In other embodiments, the fluid reservoir 134 may have a minimal size, and the plurality of reduced-pressure dressings 114 may include absorbents to hold liquids at the dressing.

The multi-port therapy unit 128 may be a collapsible unit to minimize space requirements. The multi-port therapy unit 128 may expand as it fills with liquids. In one illustrative embodiment, each reduced-pressure dressing 114 includes an absorbent layer for storing liquids in the reduced-pressure dressing 114. The absorbent layer may be made from super absorbent fibers. The super absorbent fibers may retain or bond to the liquid in conjunction with a physical or chemical change to the fibers. In one non-limiting example, the super absorbent fiber may include the Super Absorbent Fiber (SAF) material from Technical Absorbents, Ltd. of Grimsby, United Kingdom, or the like. The absorbent layer may be a sheet or mat of fibrous material in which the fibers absorb liquid from the tissue site 102. The structure of the absorbent layer that contains the fibers may be either woven or non-woven. The fibers in the absorbent layer may gel upon contact with the liquid, thereby trapping the liquid. Spaces or voids between the fibers may allow reduced pressure that is applied to the absorbent layer to be transferred within and through the absorbent layer. In one illustrative embodiment, the fiber density of the fibers in the absorbent layer may be approximately 1.4 grams per millimeter.

Optionally, a positive pressure exhaust from a vacuum pump in the reduced-pressure source 150 may be routed into channels that are pressurized at a greater pressure than the reduced pressure gradient within the fluid reservoir 134 such that the fluid reservoir 134 has a structure that inflates around it. Alternatively, the chambers may be sealed at ambient pressure, so when an aircraft transporting a patient using the system 100 reaches altitude, the reduced pressure at altitude may cause a pressure differential that fills the channels with higher pressure air.

The fluid reservoir 134 of the multi-port therapy unit 128 may include a tortuous path such that fluid may not easily reflux from channel to channel. This may take the form of an opening from a pathway of a second baffle, or series of baffles within a rigid section of the fluid reservoir 134. The tortuous paths may take the form of small pieces of absorbent, non-woven looking material, or a small-pore open-celled foam acting as a barrier to low pressure reflux or fluids. By having a small-pored, open foam acting as a baffle over each channel through which the fluids entering the fluid reservoir flow, one is using the "adhesive" effect of the fluid to the foam to reduce the risk of fluids within the fluid reservoir being refluxed due to small changes in pressure bias. Essentially, one would expect the fluids to prefer to stay on and within the foam structure during the period of time of any significant pressure imbalance.

There may be incorporated into the multi-port therapy unit 128 a variety of valves that allow fluid and air to flow in one direction into the fluid reservoir 134 but prevents these same fluids from reverse flow. Such valves, commonly known as check-valves, include flat/flap valves and duck-bill valves.

In one illustrative embodiment, the fluid reservoir 134 may be an absorbent pouch. The fluid reservoir may be a pouch containing an absorbent layer such as the one previously mentioned.

The supply-side port 144 may include a hydrophobic or oleophobic filter. The hydrophobic filter prevents fluids from being passed to the reduced-pressure source 150. The hydrophobic filter is periodically changed. The hydrophobic filter may be included as part of a fluid reservoir 134 and replaced when the fluid reservoir 134 is replaced. If the fluid reservoir 134 becomes full, at times it may be desirable to drain some of the liquids therein. For this reason, the valve 137 may be opened and fluids removed through the drain conduit 135. If reduced pressure therapy is occurring during the draining process, a valve that prevents reduced pressure from entering the supply-side port 144 may be incorporated and used to prevent the bleeding of reduced pressure. If the fluid reservoir 134 includes an absorbent in the fluid reservoir 134, an osmotic membrane may be used to have a fluid gathering section that allows easy draining of that portion. In other words, water is separated from the exudate such that the water may be discarded.

The ports 130, 144 may be configured to be "connector-less" connections. Shut-off valves may be incorporated into the connectors to minimize loss of vacuum during connecting and disconnecting.

In an alternative embodiment, the pressure sensors 132 may be removed from the multi-port therapy unit 128 and placed on the plurality of reduced-pressure dressings 114. This may be more desirable with inexpensive pressure sensors. Such an approach would, eliminate the need for blockage detectors and allow specific tissue site pressure monitoring with more accuracy. The fluid reservoir 134 may be removed from the multi-port therapy unit 128 for disposal. This leaves the remaining components for refurbishing and reuse according to one illustrative embodiment.

Figure 3:
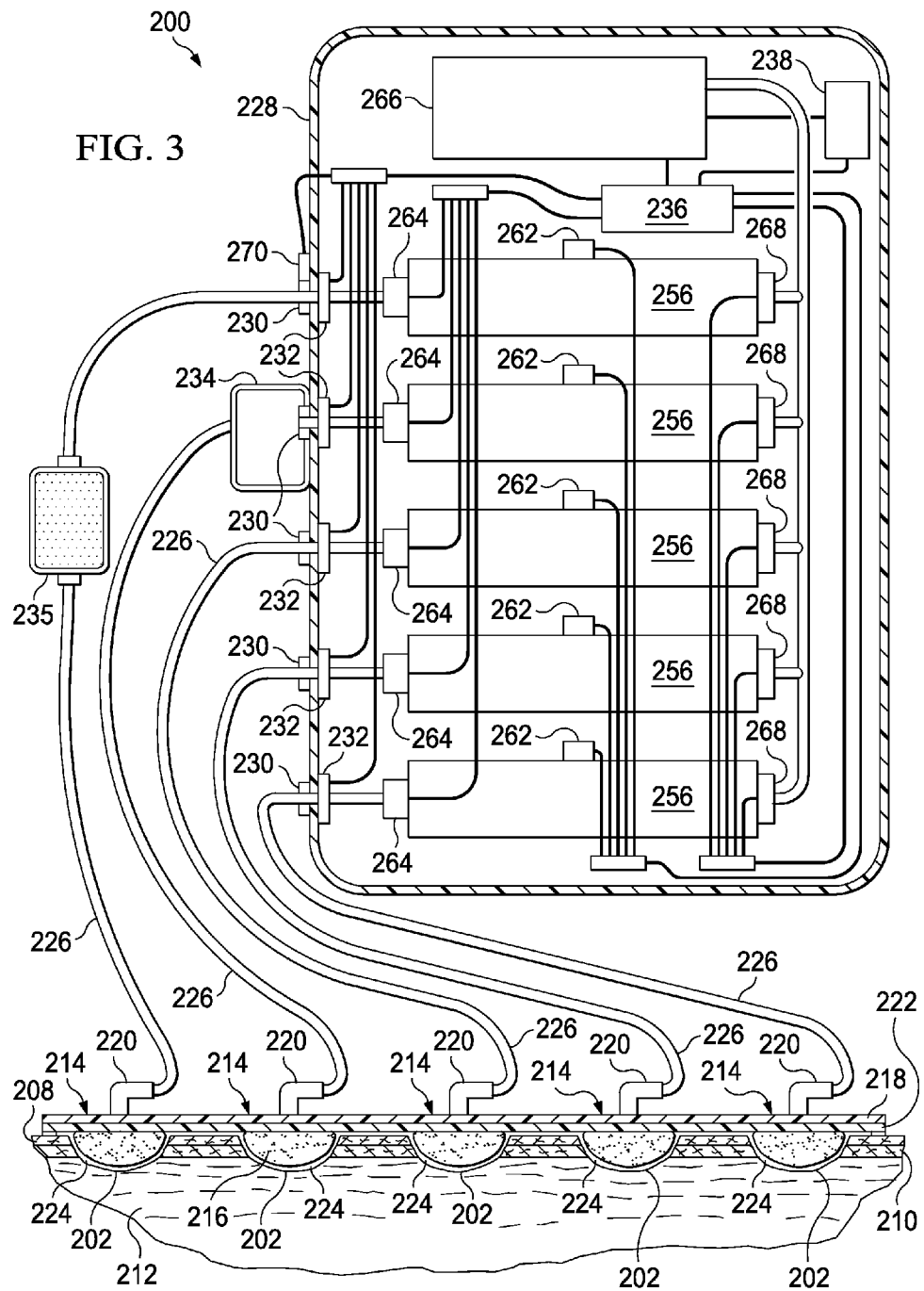
FIG. 3 is a cross-sectional view (with a portion shown as a schematic diagram) of an illustrative embodiment of a system for simultaneously treating a plurality of tissue sites on a patient.

Referring now primarily to FIG. 3, another illustrative embodiment of a system 200 for simultaneously treating a plurality of tissue sites 202 is presented. The plurality of tissue sites 202, plurality of reduced-pressure dressings 214, and many other aspects of the system 200 are analogous to those in FIG. 1. While numerous tissue sites, sizes, and depths may be treated with the system 200, the system 200 is shown treating tissue sites 202 in the form of wounds. The wounds are shown for illustrative purposes extending through epidermis 208, dermis 210, and into subcutaneous tissue 212. Other depths or types of wounds or, more generally, tissue sites may be treated. While five tissue sites 202 are shown for illustration purposes, it should be understood that any number of tissue sites—typically two and greater—may be treated with the system 200.

The system 200 includes the plurality of reduced-pressure dressings 214 deployed on the plurality of tissue sites 202. Each of the plurality of reduced-pressure dressings 214 may be any kind of dressing that allows reduced pressure to be delivered to the tissue site 202 associated with the reduced-pressure dressing 214 and that is operable to remove fluids from the tissue site 202. In one illustrative embodiment, each reduced-pressure dressing 214 includes a manifold 216, a sealing member 218, and a reduced-pressure interface 220. The sealing member 218 is releasably coupled to the tissue site 202 using an attachment device 222. The attachment device 222 may take numerous forms, such as those previously mentioned. The sealing member 218 creates a sealed space 224 containing the manifold 216 and the tissue site 202 to be treated. These components are analogous to those in FIG. 1.

The reduced-pressure dressings 214 are fluidly coupled to a multi-port therapy unit 228 by a plurality of multi-lumen reduced-pressure delivery conduits 226. Each multi-lumen reduced-pressure delivery conduit 226 may include at least one pressure-sampling lumen and at least one reduced-pressure supply lumen. Each multi-lumen reduced-pressure delivery conduit 226 has a first end 227 and a second end 229. The first ends 227 are fluidly coupled to the multi-port therapy unit 228 at a plurality of patient-side ports 230. As in FIG. 1, each patient-side port 230 that is not used may have a cap (see 131 in FIG. 1) covering the patient-side port. Each of the plurality of patient-side ports 230 is configured to fluidly couple with one of the plurality of multi-lumen reduced-pressure delivery conduits 226 and have at least one of the pressure-sampling lumens and one of the reduced-pressure supply lumens fluidly coupled. The pressure-sampling lumen is fluidly coupled to one of a plurality of treatment pressure sensors 232.

A fluid storage device is fluidly coupled to each of the plurality of multi-lumen reduced-pressure delivery conduits 226. The fluid storage device is fluidly coupled to the plurality of reduced-pressure dressings 214 for receiving and at least temporarily storing fluids therefrom. The fluid storage device may be one or more of the following: a single reservoir (not explicitly shown but analogous to 134 in FIGS. 1-2) fluidly coupled to each the multi-lumen reduced-pressure delivery conduits 226, a plurality of fluid reservoirs 234 (only one is shown for illustration purposes) associated with the multi-port therapy unit 228, a plurality of in-line canisters 235 (only one is shown for illustration purposes), a plurality of sections within one large canister which are specific to each wound, or a plurality of absorbent layers associated with or forming part of the plurality of reduced-pressure dressings 214.

The multi-port therapy unit 228 includes a controller 236, the plurality of patient-side ports 230, and a plurality of reduced-pressure plenums 256. Each of the plurality of reduced-pressure plenums 256 is associated with one of the plurality of patient-side ports 230. Each plenum of the plurality of reduced-pressure plenums 256 is a pressure vessel for holding reduced pressure. Each plenum may have a fixed volume or a variable volume. With respect to the latter, as shown in FIG. 4, in one illustrative embodiment, each plenum of the plurality of reduced-pressure plenums 256 may be formed with a moveable wall 258 that is biased outward by biasing devices 260 to help maintain reduced pressure in the interior of the reduced-pressure plenum 256. The biasing device 260 may be a spring compressed shorter than its free length, a positively charged cylinder, or other biasing device. Each plenum may have a fixed volume between about 50 cc and about 400 cc, for example.

The multi-port therapy unit 228 also includes the plurality of treatment pressure sensors 232. Each of the plurality of treatment pressure sensors 232 is associated with one of the plurality of patient-side ports 230 for determining a pressure associated with at least one pressure-sampling lumen in the multi-lumen reduced-pressure delivery conduit 226 associated with the patient-side port 230. Each treatment pressure sensor 232 is operatively coupled to the controller 236 to provide a treatment pressure signal to the controller 236.

The multi-port therapy unit 228 also includes a plurality of plenum pressure sensors 262. Each of the plurality of plenum pressure sensors 262 is associated with one of the plurality of reduced-pressure plenums 256 and is operatively coupled to the controller 236 for supplying a plenum pressure signal.

The multi-port therapy unit 228 also includes a first plurality of control valves 264 fluidly coupled between each of the plurality of reduced-pressure plenums 256 and an associated patient-side port 230. The plurality of first control valves 264 may comprise a plurality of proportional valves. Each of the first plurality of control valves 264 is operatively coupled to the controller 236 so that each of the first plurality of control valves 264 may be controlled by the controller 236. The first plurality of control valves 264 controls the delivery of reduced pressure from the reduced-pressure plenums 256 into the plurality of multi-lumen reduced-pressure delivery conduits 226. A bacteria filter may be associated with each of the first plurality of control valves 264. Alternatively or in addition, a bacteria filter may be placed at the ports 230 or if an in-line canister is used as part of that structure.

The multi-port therapy unit 228 also includes a main vacuum source 266 fluidly coupled to each of the plurality of reduced-pressure plenums 256 for charging the reduced-pressure plenums 256, i.e., supplying reduced pressure to each of the plurality of reduced pressure plenums 256. The main vacuum source 266 is typically a single vacuum pump but could also be a wall supply of reduced pressure or a multi-pump subsystem. If a vacuum pump, the main vacuum source 266 may receive electrical power from an electrical power source 238. The main vacuum source 266 can charge each of the plurality of reduced-pressure plenums 256 with reduced pressure. The stored reduced pressure is used to deliver regulated reduced pressure to the tissue sites 202. In one illustrative embodiment, the reduced pressure in each reduced-pressure plenum 256 is greater (more negative on a pressure scale) than −400 mm Hg.

The multi-port therapy unit 228 also includes a second plurality of control valves 268 fluidly coupled between each of the plurality of reduced-pressure plenums 256 and the main vacuum source 266. The plurality of second control valves 268 may comprise proportional valves. The second plurality of control valves 268 controls the introduction of reduced pressure into the reduced-pressure plenums 256. The second plurality of control valves 268 may have a hydrophobic filter associated with each to prevent liquids from reaching the main vacuum source 266.

Each of the plurality of first control valves 264 is controlled to regulate the reduced pressure down to the pressure selected by the caregiver for a respective channel and tissue site 202. Optionally, the multi-lumen reduced-pressure delivery conduits 226 or connector may include an automatic shut-off valve to isolate an individual line for a dressing change without interacting with the user interface associated with the controller 236. An indicator could be provided on each line to help isolate leaks—one implementation may be a green/yellow/red indicator that is based on the controller's calculation of recharge rate for a given plenum module, in conjunction with information about the proportional valve set point required to maintain the selected therapy reduced pressure. Multi-lumen reduced-pressure delivery conduits 226 may be color-coded to aid in therapy management.

The controller 236 may be a printed wire assembly (PWA), for example, or an application specific integrated circuit (ASIC) with a microprocessor and memory or other control device. The controller 236 is operative to regulate the reduced pressure supplied from the plurality of reduced-pressure plenums 256 to the plurality of patient-side ports 230 by controlling the first plurality of control valves 264 and to regulate the reduced pressure supplied to the plurality of reduced-pressure plenums 256 using the second plurality of control valves 268. The controller 236 is electrically coupled to the electrical power source 238.

In one illustrative embodiment, the controller 236 is configured to receive the plenum pressure signal for each plenum of the plurality of reduced-pressure plenums 256, and if a plenum pressure signal is less than a plenum threshold (for example, without limitation, if −290 mm Hg is less reduced pressure than an illustrative plenum threshold of −300 mm Hg) to at least partially open the associated valve of the second plurality of control valves to deliver additional reduced pressure to the plenum associated with the plenum pressure signal that is less than the plenum threshold. The controller 236 is also configured to receive the treatment pressure signal for each of the plurality of treatment pressure sensors 232 and if a treatment pressure signal is less than a minimum treatment pressure threshold (e.g., without limitation, the pressure is −90 mm Hg which is less than the minimum treatment pressure of −100 mm Hg) to at least partially open the associated valve of the first plurality of control valves 264 and if the treatment pressure signal is greater than a high treatment pressure threshold to at least partially close the associated valve of the first plurality of control valves 264. Each of the plurality of patient-side ports 230 may also include a relief valve to limit the maximum reduced pressure that may be applied to a reduced-pressure dressing 214.

The controller 236 may also be operative to prioritize the filling of the plenums of the plurality of reduced-pressure plenums 256 such that a plenum having a plenum pressure signal that over time continues below a plenum threshold will be filled only after other plenums of the plurality of reduced-pressure plenums 256. In other words, if the controller 236 determines that a leak may be occurring with a reduced-pressure dressing 214 or other aspect associated with a particular plenum, that plenum will be filled last to avoid devoting all or a substantial amount of the system's reduced pressure to trying to compensate for a leak.

A plurality of indicators 270 (only one shown for illustration purposes) may be associated with each of the patient-side ports 230. The indicators 270 may be LED lights or other visual indicators. If the controller 236 determines that a leak may exist as referenced above, the controller 236 may cause the indicator 270 associated with the channel or particular reduced-pressure dressing 214 to be activated. In this way, the user may be able to address the leak for that particular channel or reduced-pressure dressing 214.

Numerous alterations and options may be exercised with the system 200. In another illustrative embodiment, the system 200 may be used with a different arrangement of reduced-pressure plenums 256 such that perhaps two channels are operated on one plenum or the system has one larger plenum upon which each channel is fed.

The volume of a reduced-pressure plenum 256 may vary (depending upon the capacity one wishes to provide and the likely leak tolerance one needs the system to manage) from about 50 cc at the low end to about 400 cc. Other volumes are possible.

In another illustrative embodiment, the reduced-pressure plenum 256 is adjusted to use mechanical pressure/energy storage. For example, a sealed bellow plastic structure of sufficient strength that it is able to vertically or in some form collapse under a vacuum that is also capable of exerting force to return to its previous shape may be used. In this case, the force is essentially multiplied. If one considers such a structure with a spring structure incorporated (see FIG. 4), under high reduced pressure the air is removed and the structure is charged. When connected to the wound via the regulating valves, the spring attempts to extend and the structure will expand to 'pump' negative pressure to the wound. The pressure in the structure or the mechanical position of the structure may be monitored in order to determine when a re-charge is required. This may be a molded bellows structure or a piston type assembly with a central spring, or alternatively a combination of the aforementioned structures with constant force springs such that the pressure delivered is predictable.

In another illustrative embodiment, the main vacuum source 266 may be used in conjunction with or replaced with a connection to another pump such as wall-suction or another integrated vacuum source which would be available at the place of treatment. Such a system would have the advantage of requiring less electrical power during operation and would in the case of an airborne system be reliant on other flight approved pumps.

In another illustrative embodiment where the user does not require a change of the regulated pressure setting for each wound, the proportional valves may be replaced with a simple mechanical regulating valve which controls the wound pressure. This arrangement would still provide for pressure feedback and alarms. With an absorbent based dressing system, there will be no tube blockages so the system may merely determine and confirm the appropriate delivery of pressure and also notify the caregiver when the dressing is full.

Further, if a mechanical valve is used, the valve may be manufactured and produced such that it is capable of selecting from a range of pressures. Such a design might include a rotational collar on the regulating valve, which would adjust the spring force on the regulating diaphragm such that with less force, a lower pressure is regulated to the wound, and with a greater force on the diaphragm, a higher pressure is regulated to the wound. The electronic system may be configured to recognize that this pressure has been manually adjusted to either pre-set levels (e.g., −75/−125/−200 mm Hg) or to a user selected variable pressure (−143 mm Hg for example) by a pressure sensor connected to the immediate orifice of the regulator and thus provide pressure feedback in the knowledge that this pressure is the pressure which should be manifolded to the reduced-pressure interface through the absorbent structure.

In another illustrative embodiment, the higher-vacuum plenum volume could include the multi-lumen reduced-pressure delivery conduit 226 going to the wound site, with final pressure regulation and wound pressure sensing hardware placed at or near each tissue site 202. Regulation would be implemented with a piezo-proportional valve (e.g., from Festo) which requires relatively little battery power (small currents are required only to change the valve opening, not to maintain a setting). Disposable medical grade pressure sensors (e.g., from Measurement Specialties) are available at low cost to incorporate into the dressing. Wireless communication back to the controller 236 is possible, and this would provide additional options for using y-connectors to reduce the number of tube sets running back to the main control unit, and thus reduce the number of plenums required.

In one illustrative embodiment, light may be used to identify channels with issues. It has been shown that clear extruded tubing makes a good conduit for light transmission. This can be utilized to highlight individual conduits by applying a light source to one end, which has the effect of illuminating the length of conduit much like a fiber optic tube, but in this instance the light diffuses along its length. This may also be helpful in instructing the user of the location of a fluid or exudate blockage, as one would expect that the transmitted light would be refracted less after such a mass. This would be useful to indicate which one of multiple conduits is at issue during a fault condition or when setting up the system. As it is expected that the device may be used in noisy environments such as field hospitals and military aircraft, this feature may augment the audio feedback that is often relied upon during modes such as seal check. The use of multi-color LEDs would allow for the color to be altered depending on the information that was being communicated.

Figure 5:
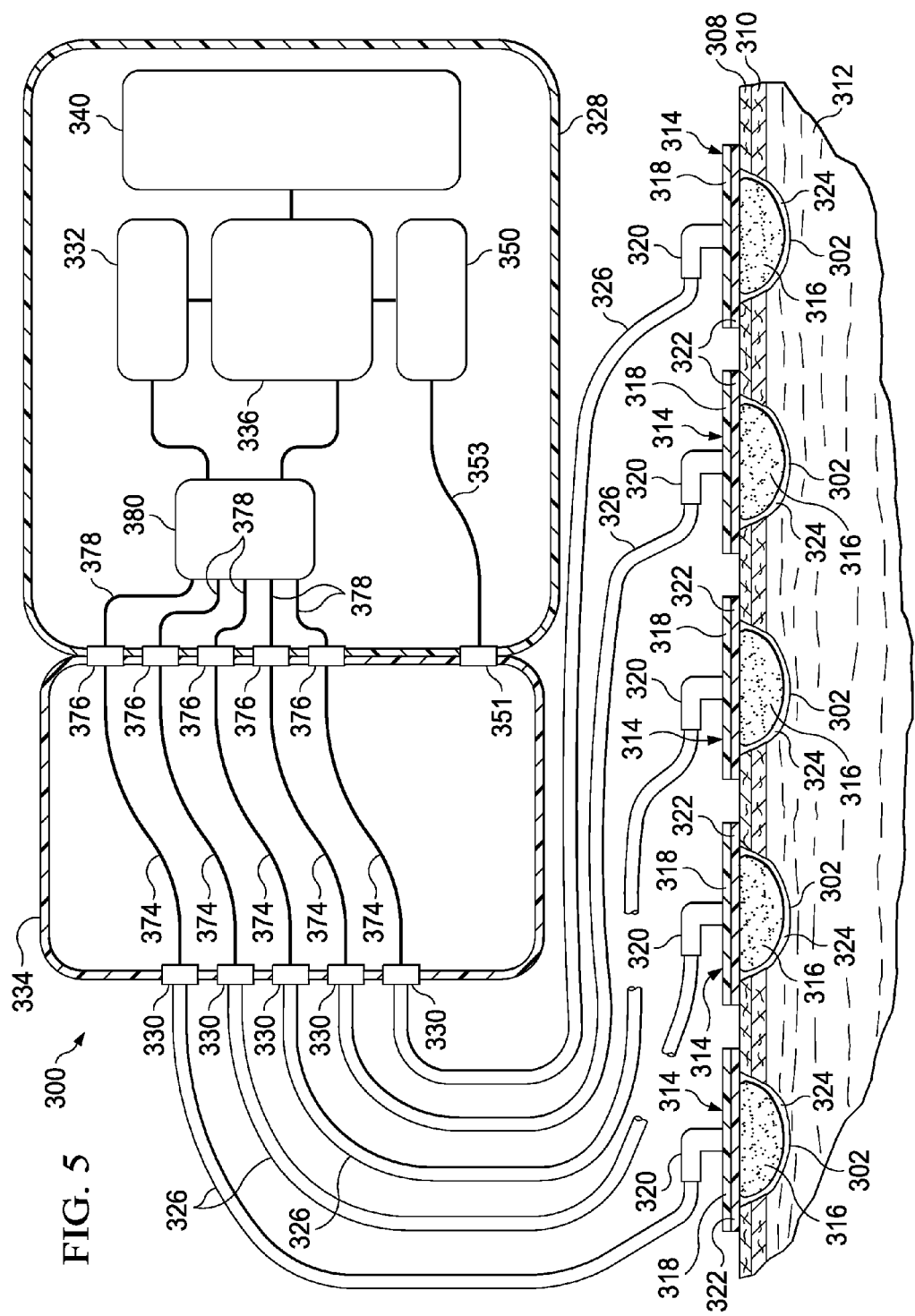
FIG. 5 is a cross-sectional view (with a portion shown as a schematic diagram) of an illustrative embodiment of a system for simultaneously treating a plurality of tissue sites on a patient.

Referring now primarily to FIG. 5, an illustrative embodiment of a system 300 for simultaneously treating a plurality of tissue sites 302 on a patient 304 is presented. The plurality of tissue sites 302, plurality of reduced-pressure dressings 314, and many other aspects of the system 300 are analogous to those in FIGS. 1 and 4. While numerous tissue sites, sizes, and depths may be treated with the system 200, the system 300 is shown treating tissue sites 302 in the form of wounds. The wounds are shown for illustrative purposes extending through epidermis 308, dermis 310, and into subcutaneous tissue 312. Other depths or types of wounds or, more generally, tissue sites may be treated. While five tissue sites 302 are shown for illustration purposes, it should be understood that any number of tissue sites—typically two or greater—may be treated with the system 300.

The system 300 includes the plurality of reduced-pressure dressings 314 deployed on the plurality of tissue sites 302. Each of the plurality of reduced-pressure dressings 314 may be any kind of dressing that allows reduced pressure to be delivered to the tissue site 302 associated with the reduced-pressure dressing 314 and that is operable to remove fluids from the tissue site 302. In one illustrative embodiment, each reduced-pressure dressing 314 includes a manifold 316, a sealing member 318, and a reduced-pressure interface 320. The sealing member 318 is releasably coupled to the tissue site 302 using an attachment device 322. The attachment device 322 may take numerous forms, such as those previously mentioned in other embodiments. For each tissue site 302, the sealing member 318 creates a sealed space 324 containing the manifold 316 and the tissue site 302 to be treated. These components are analogous to those in FIGS. 1 and 4.

The reduced-pressure dressings 314 are fluidly coupled to a fluid reservoir 334. The fluid reservoir 334 has a plurality of patient-side ports 330 that are fluidly coupled to a plurality of multi-lumen reduced-pressure delivery conduits 326. The fluid reservoir 334 is fluidly coupled to a reduced-pressure source 350 through a reduced-pressure port 351. An internal conduit 353 is fluidly coupled between the reduced-pressure port 351 and the reduced-pressure source 350. A plurality of by-pass conduits 374 fluidly coupled the pressure-sampling lumens of the multi-lumen reduced-pressure delivery conduits 326 to a plurality of pressure ports 376. A plurality of internal conduits 378 fluidly couples the plurality of pressure ports 376 to a multiplexing valve 380. Alternatively, a plurality of control valves may be used on a plurality of internal conduits fluidly coupling the plurality of pressure ports 376 and treatment pressure sensor 332. A controller 336 can close all the valves except one at a time to use the treatment pressure sensor 332 on each valve. The treatment pressure sensor 332 is operatively coupled to the controller 336 to deliver treatment pressure signals.

A fluid storage device is fluidly coupled to each of the plurality of multi-lumen reduced-pressure delivery conduits 326. The fluid storage device is fluidly coupled to the plurality of reduced-pressure dressings 314 for receiving and at least temporarily storing fluids therefrom. The fluid storage device may be one or more of the following: the fluid reservoir 334 fluidly coupled to each the multi-lumen reduced-pressure delivery conduits 326 as shown, or a plurality of in-line canisters (not shown but analogous to in-line canister 235 in FIG. 4)), or a plurality of absorbent layers associated with or forming part of the plurality of reduced-pressure dressings 314.

The multi-port therapy unit 328 includes the controller 336 and the plurality of pressure ports 376. Each of the plurality of pressure ports 376 is configured to fluidly couple with at least one of the pressure-sampling lumens of the plurality of multi-lumen reduced pressure delivery conduits 326. The multi-port therapy unit 328 further includes the treatment pressure sensor 332 that is fluidly coupled to the plurality of pressure-sampling lumens associated with the plurality multi-lumen reduced-pressure delivery conduits 326. A valve means may be used to couple one of the plurality of pressure ports 376 to the treatment pressure sensor 332 at a time. The valve means may be the multiplexing valve 380 or plurality of valves as described elsewhere herein.

The multi-port therapy unit 328 also includes the reduced-pressure source 350 that is fluidly coupled to the plurality of reduced-pressure dressings 314. The reduced-pressure source 350 is operatively coupled to the controller 336. The reduced-pressure source 350 charges the fluid reservoir 334 with reduced pressure that is delivered by the plurality of multi-lumen reduced-pressure delivery conduits 326 to the plurality of reduced-pressure dressings 314.

The multi-port therapy unit 328 also includes the controller 336. The controller 336 is operatively coupled to the treatment pressure sensor 332, the valve means (e.g., multiplexing valve 380), and the reduced-pressure source 350. The controller 336 is configured to monitor the treatment reduced pressure signals of each of the plurality of pressure-sampling lumens associated with the plurality of multi-lumen reduced-pressure delivery conduits 326 as measured by the treatment pressure sensor 332. In response, the controller 336 controls the reduced pressure delivered by the reduced-pressure source 350 to the plurality of reduced-pressure dressings 314. The controller 336 may be configured to determine a number of pressure ports 376 in use and to look up a gross-flow-rate limit for the number and compare the gross-flow-rate limit to the actual flow rate of the reduced-pressure source 350 and if the actual flow rate is greater than the gross-flow-rate limit, to activate an alert (audible alarm, visual indicator, or other alert). As described further below, the controller 336 may be configured to use various steps to determine if one or more of the reduced-pressure dressings 314 is leaking. A user interface 340 may be used to receive information from or to input commands or data into the controller 336.

Figure 6:
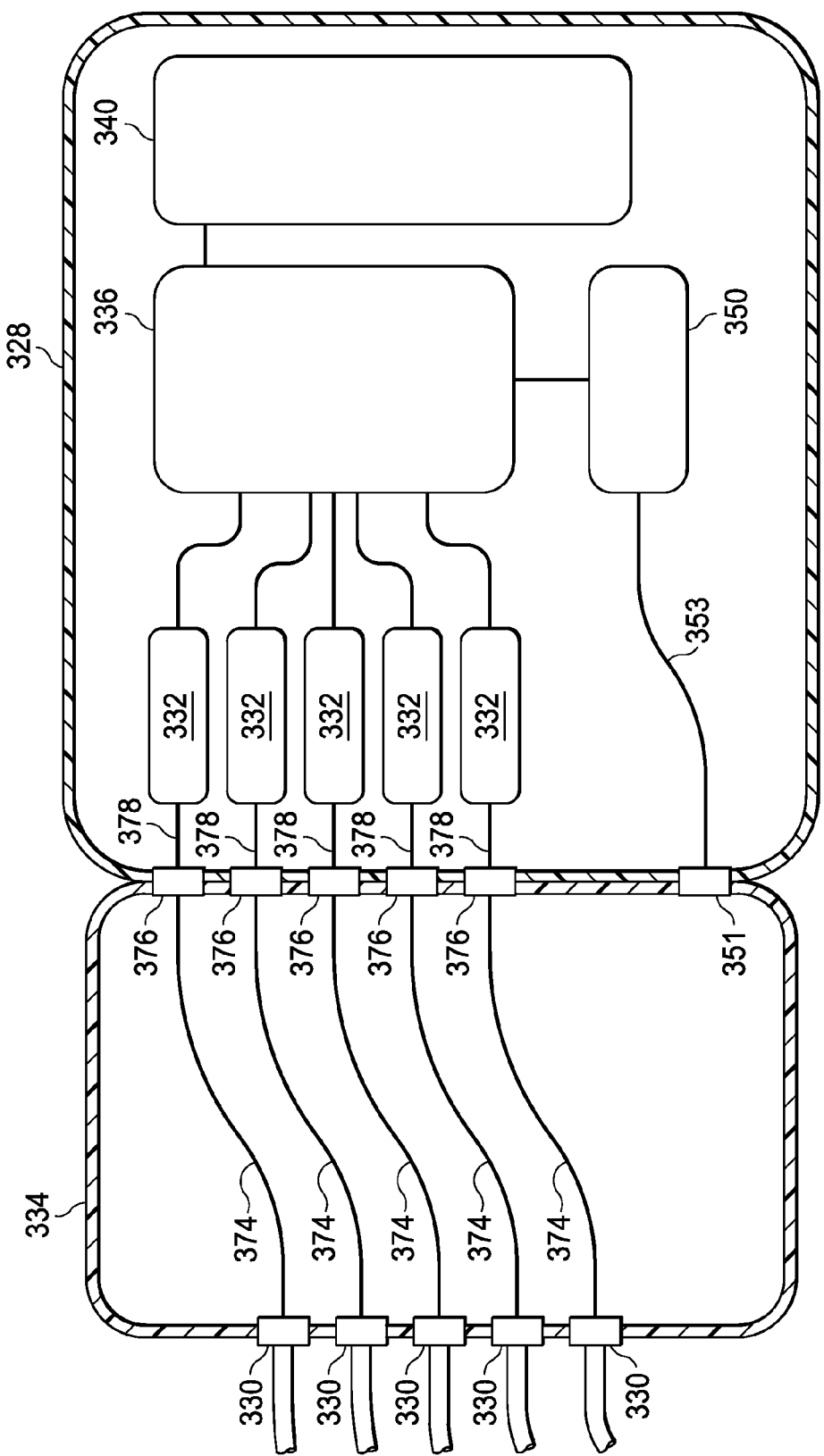
FIG. 6 is a schematic diagram of a portion of an illustrative embodiment of a system for simultaneously treating a plurality of tissue sites on a patient.

Referring now primarily to FIG. 6, another illustrative embodiment of a portion of a system 300 for simultaneously treating a plurality of tissue sites 302 on a patient is presented. The system 300 of FIG. 6 is analogous to the system 300 of FIG. 5 and accordingly some components are labeled with reference numerals but not further described here. FIG. 6 differs mainly in that instead of a single treatment pressure sensor 332, a plurality of treatment pressure sensors 332 are used. The plurality of pressure ports 376 are fluidly coupled to the plurality of treatment pressure sensors 332, which each develop a treatment pressure signal. The plurality of treatment pressure sensors 332 are operatively coupled to the controller 336 for delivering the treatment pressure signals to the controller 336. Other aspects of the system 300 are analogous to FIG. 5.

Figure 7:
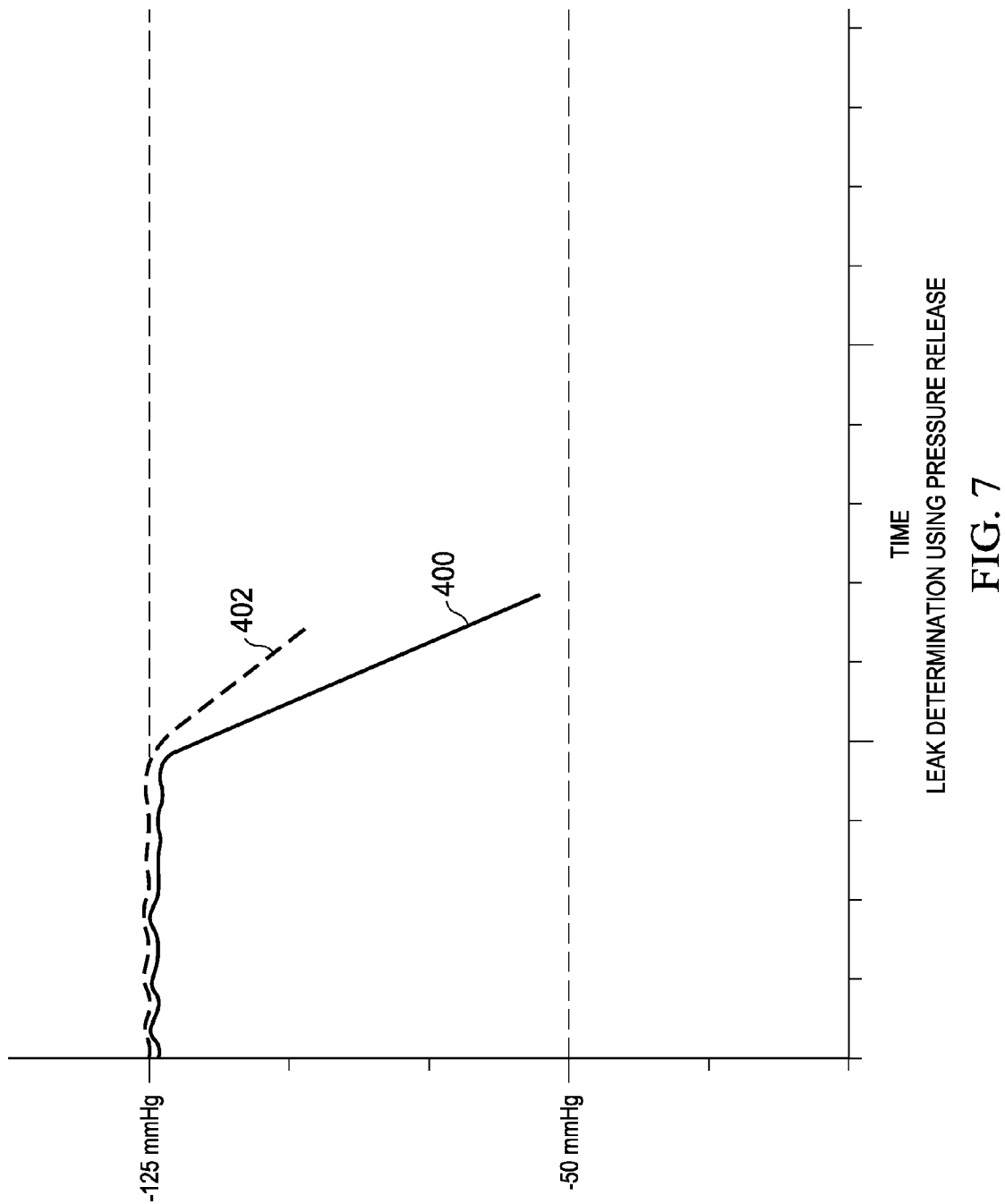
FIG. 7 is a schematic pressure-time graph for illustrating a method for identifying a leak in system for simultaneously treating a plurality of tissue sites on a patient.
Figure 8:
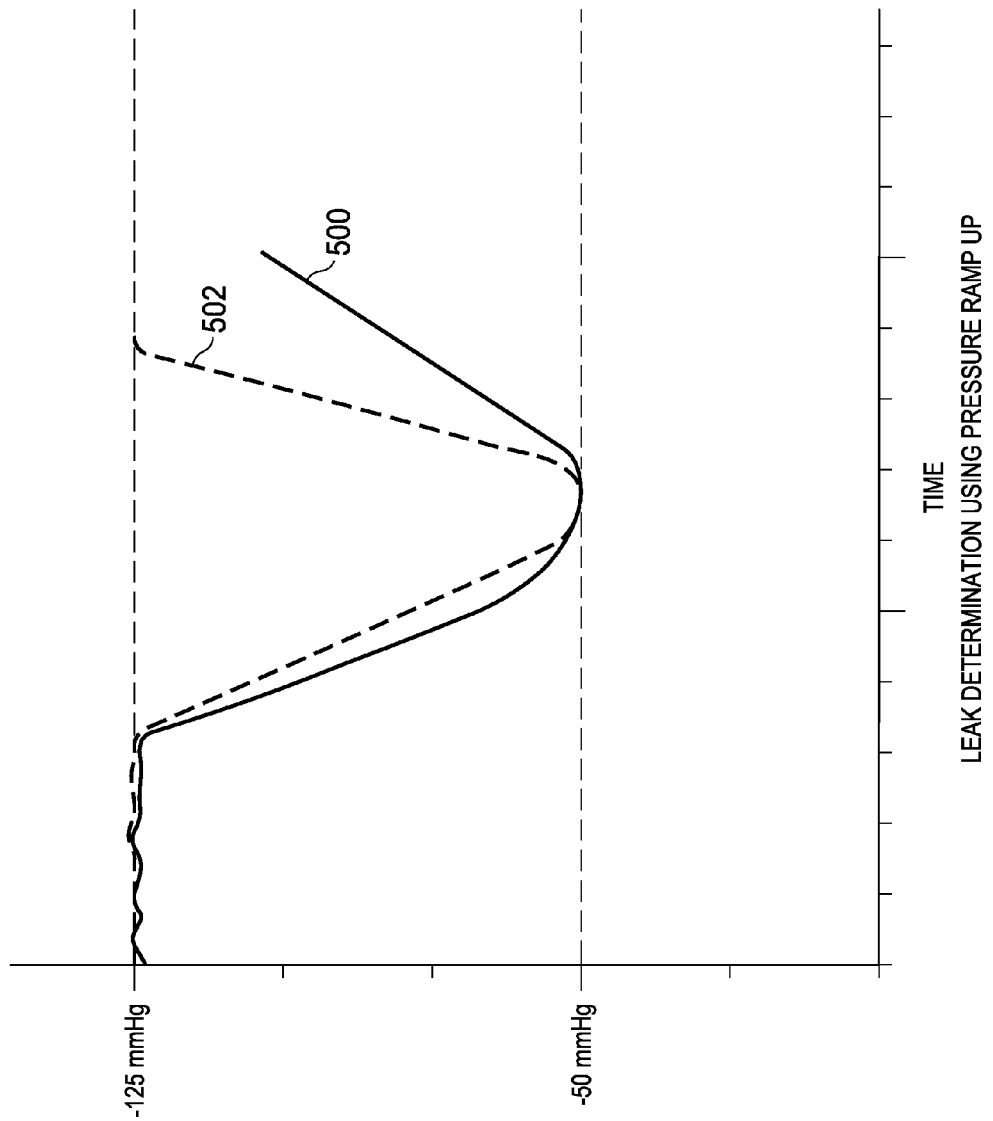
FIG. 8 is a schematic pressure-time graph for illustrating a method for identifying a leak in a system for simultaneously treating a plurality of tissue sites on a patient.

With respect to both FIGS. 5 and 6 and other embodiments, a number of approaches may be used in configuring the controller 336 to determine when a leak likely exists. Two prominent approaches are readily used. With reference to FIG. 7, the first includes stopping the reduced pressure to the reduced-pressure dressings 314 and then comparing its decay pattern 400 to a set standard or a median decay pattern 402. If the variation is greater than a desired threshold, the controller 336 activates an alert. With references to FIG. 8, the second approach is to stop the reduced pressure supplied to the reduced-pressure dressing 314 for a time period and then to activate the reduced pressure and capture the ramp-up pattern 500 for a particular reduced-pressure dressing 314. This approach may be combined with the initial pressure decay test to provide dual confirmation of the leaking channel. The ramp-up pattern 500 may then be compared to a standard or median pattern 502.

In most illustrative embodiments, the controller 336 may begin with a process of auto-detection in which wounds are connected by measuring the on-set of pressure during pull down. Each channel is isolated by a sealing valve or membrane at the connection port that is opened on application of the wound care disposable. If a channel is found to not be responding, the user is informed at the start of therapy to that the channel is not connected (cannot be a leak as all channels will be low). The system takes the number of dressings connected into account when it determines the leak alarm threshold (e.g., 1 wound=1 l/min at 125 mmHg, 5 wounds=2 l/min at 125 mm Hg, and proportional to the number of wound ports connected).

To prevent reflux of fluids from the fluid reservoir 334 to the multi-lumen reduced-pressure delivery conduits 326, a simple blocking feature may be added, such as a piece of open-celled foam, across the entry ports 330 so that fluid splashes do not have the opportunity of reaching the opening but fluids can be drawn into the fluid reservoir 334. As there is a typically a pressure gradient through the system 300 with the greater reduced pressure in the fluid reservoir 334 and reducing down towards the dressing 314, it is not anticipated that flow will naturally occur towards the dressing 314. Alternatively or in addition, a simple flap valve could be constructed at the port 330 from a material that is permeable to fluids so that therapy is not compromised but will resist an instantaneous burst of fluid as could happen if the fluid reservoir 334 was agitated or knocked over.

With reference again primarily to FIG. 5, according to an illustrative embodiment, a single pressure sensor 332 is controlled and multiplexed to measure pressure in a pressure-sampling lumen of each multi-lumen reduced-pressure conduit in sequence. The controller 336 will automatically assign a percentage of sensor time to each wound, and via a directional control valve (such as an electronically actuated piston or spool valve) will pneumatically connect the sensor to each wound every 2 seconds (sample time may vary). The pneumatic volume between the valve and the sensor may be minimized to reduce the potential for the channels to be influenced by each other at switching. Initially this may be on a purely sequential basis (i.e. wound 1, wound 2, etc), but as the system 300 runs its tests, the system 300 may determine that some wounds are struggling to maintain pressure more than others, which are remaining consistent. At this time the controller may choose to prioritize these low performing wounds for more regular checks (i.e. wound 1, wound 2, wound 3, wound 2, wound 4, wound 2 . . . wound 2 has a lower pressure). Having one pressure sensor does mean that any sensor-to-sensor variances will not be a factor when the system is trying to balance the wound pressure control. The control valve switching sequence may be coordinated with a purge function in order to avoid concerns of possible cross-contamination during switching, but also to reduce the total number of valves required.

Referring again primarily to FIG. 6, according to one illustrative embodiment, a plurality of treatment pressure sensors 332 are multiplexed into one sensor port on the controller 336 which are electronically scanned by the controller in a manner similar to those previously discussed. Sensor to sensor variances may be a factor in the reporting of channel pressures, but there is a benefit here in that a failure of any one pressure sensor can be reported and that channel indicated as off to the user. In another illustrative embodiment, instead of multiplexing the signals from the treatment pressure sensors 332, the controller 336 may monitor each signal continuously.

In an illustrative embodiment, the controller 336 monitors wound pressure measured by the pressure sensor(s) via any of the methods above and determines if there is a blockage in the communication of pressure from the fluid reservoir 334 to the tissue site 302. In the instance of the use of an absorbent dressing or in-line fluid storage, this may be used to indicate that the absorbent is full. Further, by trending the level of pressure communication reduction over time (pressure-drop), the controller 336 is capable of predicting the level of fill of the absorbent (Canister pressure−Wound pressure−Leak Overhead=Pressure Drop). By trending this pressure drop calculation on a channel-by-channel basis during therapy, the controller 336 can warn the caregiver not only when the absorbent is full, but also when it is near to being full.

In one illustrative embodiment, the system 300, which has a reduced-pressure source 350 that is a vacuum pump and fixed fluid reservoir volume, is capable of detecting a leak in one or more reduced-pressure dressings 314. The leak is determined by measuring the fluid reservoir pressure and estimating air flow based on pump duty, and comparing the estimated air flow based on pump duty to pre-determined air flow levels within the software of the air flow level that should be required for a set number of wounds.

For example and without limitation, the system 300 may have a leak tolerance of 1 l/min with one or possibly 2 wound dressings. As another example, the system 300 with up to 5 wounds may have a proportionately higher leak threshold as each dressing presents its own sealing challenge, e.g., a leak tolerance of 2 l/min. The system 300 takes the number of dressings connected into account when the controller 336 determines the leak alarm threshold (e.g., 1 wound=1 l/min at 125 mm Hg, 5 wounds=2 l/min at 125 mm Hg and proportional to the number of wound ports connected). Thus, the controller 336 is capable of providing an alarm to tell the caregiver if the net average pressure in the system is low, and that a leak likely exists due to the pump having to operate at a level consistent with there being a flow of air into the system that is above its pre-determined threshold. The system 300 is pneumatically capable of delivering therapy with up to 5 dressings or another desired number with consideration given not only due to the possibility of air leak, but also because pneumatically a high flow of fluid in the system imposes the same duty on the pump. A situation may exist where all 5 wounds are moderately exudating and there are small leaks which in themselves would not trigger a leak alarm, but combined with the fluid pressure drop results in the leak alarm threshold being triggered. Therefore, the trigger level may be varied by user input.

In some illustrative systems, the pump control and the multi-channel wound pressure measurements are used to determine which dressings have the most significant leak. Essentially, this system monitors the wound pressure during deliberate dynamic changes in pump pressure to look for differences in the ways in which wound pressure changes between dressings, to seek ways to identify which one possesses an air leak, for example, as described with respect to FIGS. 7 and 8.

In another illustrative embodiment, a two-cavity (or two-chamber) canister, where the cavity acts as a plenum to allow the user to have two groups of wounds at different pressures, may be used Valves are used to allow the single pump to control pressure in these two chambers.

In another embodiment that is an alternative to FIG. 5, which uses one multiplexing valve 380, each conduit may have its own electronically actuated valve which is driven by the controller 336. When the valves are closed, they seal the line to prevent leaks. These valves may be driven directly from the main controller 336 or by a secondary PWA which has an encoder circuit driven by a serial connection from the controller PWA. This would then allow a leaking dressing to be isolated while therapy is maintained to the others until the user has corrected the fault.

The embodiments shown in FIGS. 5 and 6 feature collection of fluids in a centralized fluid reservoir 334. The use of a wound-site or an in-line absorbent component may be used to replace or augment the capacity provided by the fluid reservoir 334. This may be used where there are multiple highly exudating wounds.

In another illustrative embodiment, the systems 300 may use evaporation to further process fluids. The evaporation could be used to enhance the volume of fluids that can be accepted. A high moisture-vapor-transfer-rate (MVTR) material is used in the reduced pressure dressings 314 or at other locations. An aspect of the fluid reservoir 334 may be formed from the high MVTR material. In a pressurized cabin, it is normal for the humidity levels to be lower than 50% and for the actual pressure to be considerably lower than that experienced at sea level—both these factors will aid in the process of evaporation.

Assisting the user to identify which wound is attached to which channel or port on the canister will greatly help the user locate any wound that the device has shown to be blocked or leaking. In the simplest form, the user may simply mark the wound dressing "1", "2", "3" etc. to coincide with the port number on the fluid reservoir. In low light situations, or where there is limited time to apply dressing identification, it may not be clear which wound is connected to which canister port. Therefore each port may be fitted with a clear plastic ring that is illuminated from a light source such as a LED, which may be white or color coded for each port (i.e., a different color for each port). The light source illuminating the ring is controlled by the controller 336. The ring will either be in close proximity or touching the multi-lumen reduced-pressure delivery conduit such that a light connection is made with the conduit and that when the ring becomes illuminated light is also fed down the conduit. When an alarm is triggered for port "1", for example, the ring on that port illuminates and flashes to indicate which port is impacted, and the light will also travel down the conduit to assist in highlighting to the user which wound is involved.

Figure 9:
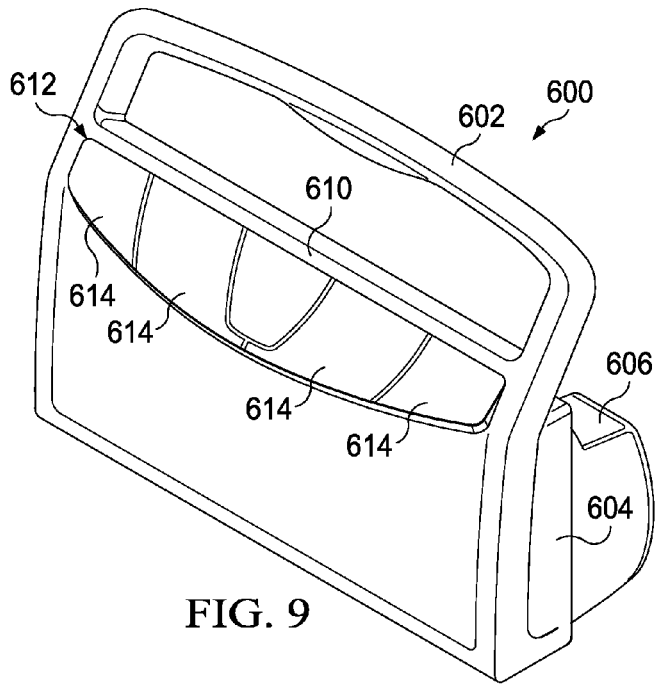
FIG. 9 is a perspective view of an illustrative embodiment of a multi-port therapy unit.
Figure 10:
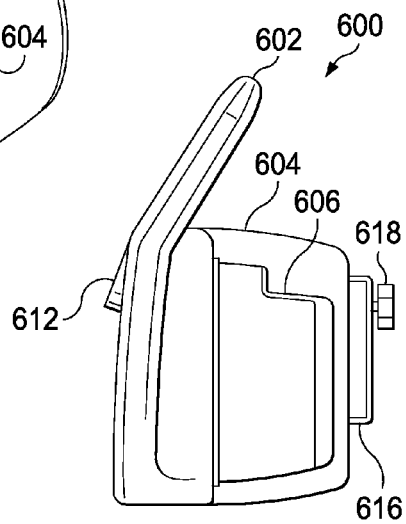
FIG. 10 is a side elevation view of the multi-port therapy unit of FIG. 9.
Figure 11:
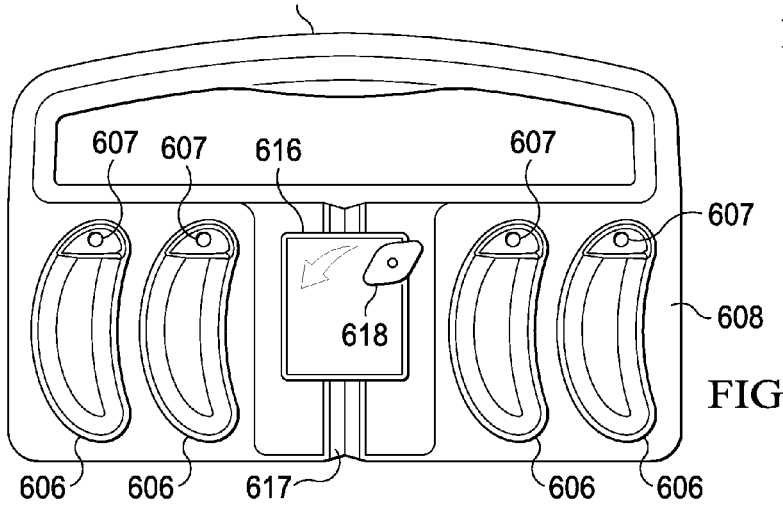
FIG. 11 is a rear elevation view of the multi-port therapy unit of FIG. 9.

The systems 100, 200, 300 or aspects of the systems for simultaneously treating a plurality of tissue sites on a patient may be structured in numerous ways. A few illustrative examples follow. Referring for example primarily to FIGS. 9-11, a multi-port therapy unit 600 is presented. The multi-port therapy unit 600 has a carrying handle 602 and a body 604. The body 604 is configured to receive a plurality of canisters 606 on a backside 608. Each canister 606 includes a fluid reservoir and a port 607 for receiving a multi-port reduced-pressure delivery conduit. The canisters 606 may include seals for interfacing with the body 604 and may clip to a support or attachment prong (not explicitly shown) or otherwise releasably attached to the body 604.

Reduced pressure is supplied from a vacuum pump within the body 604 to each canister 606. Additionally, a pressure sensor (e.g., pressure sensor 132 in FIG. 2) is fluidly coupled to the pressure-sampling lumen of the associated multi-port reduced-pressure deliver conduit. These various configurations and operational aspects may be as those previously presented for the various illustrative embodiments. A front face 610 includes a user panel 612, or user interface. The user panel 612 may have segments 614 devoted to each of the plurality of canisters 606. The back side 608 may include a pole-attachment device 616 for releasably attaching the multi-port therapy unit 600 to a pole or other securing member. The pole-attachment device 616 may include a pole channel 617 and a knob 618 to screw a clamp onto the pole in the pole channel 617 or other securing member.

Figure 12:
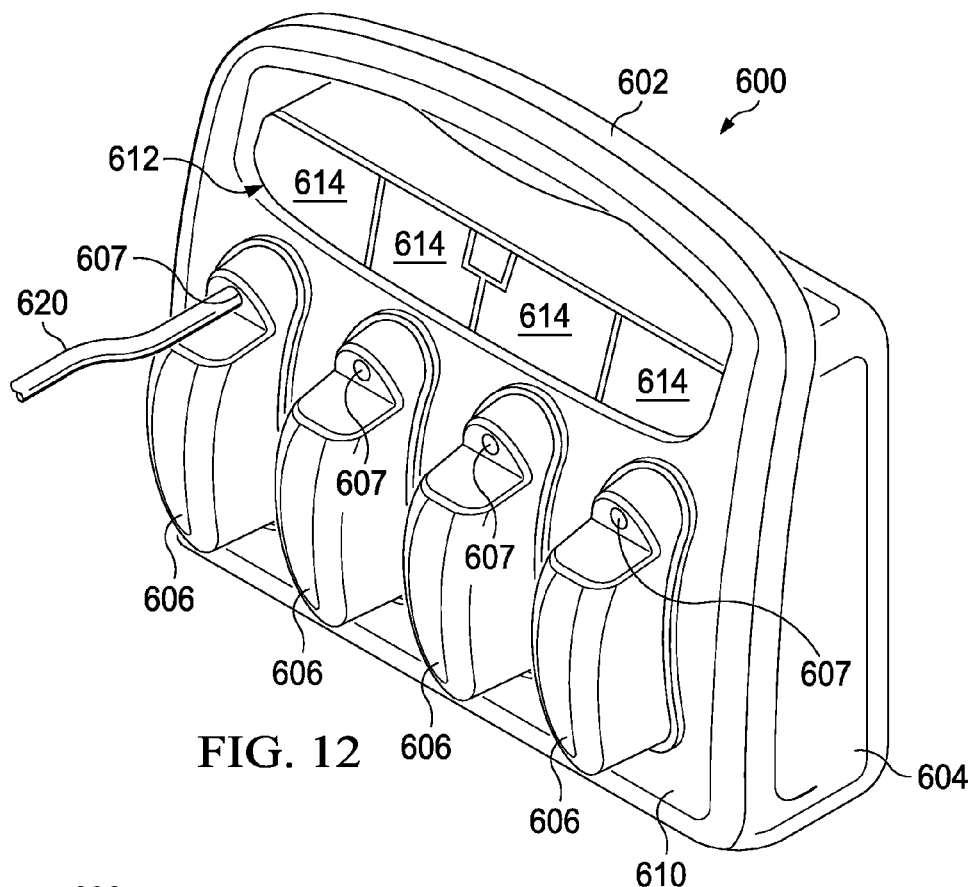
FIG. 12 is a perspective view of an illustrative embodiment of a multi-port therapy unit.
Figure 13:
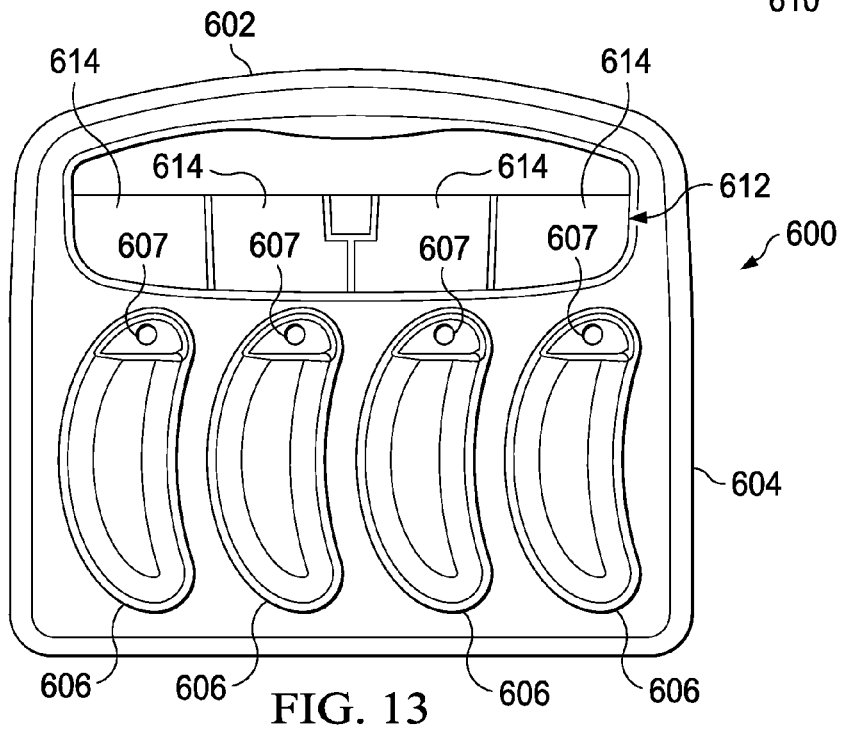
FIG. 13 is a front elevation view of the multi-port therapy unit of FIG. 12.
Figure 14:
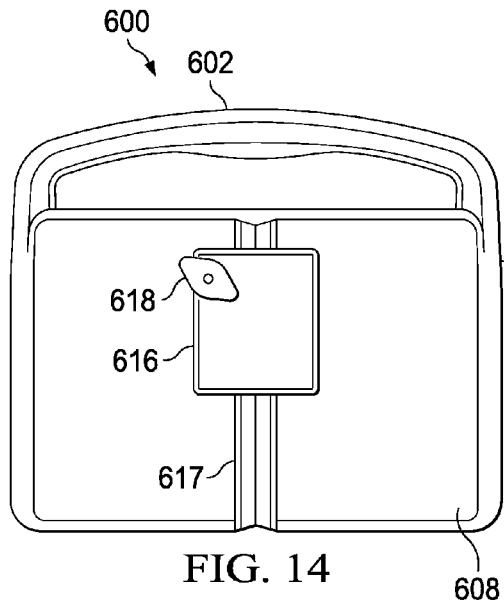
FIG. 14 is a rear elevation view of the multi-port therapy unit of FIG. 12.
Figure 15:
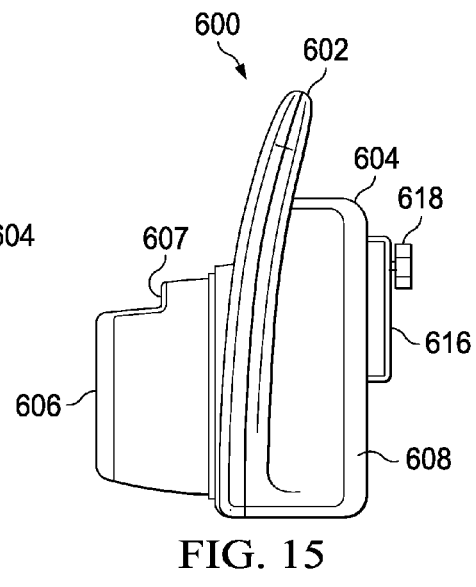
FIG. 15 is a side elevation view of the multi-port therapy unit of FIG. 12.

Referring now primarily to FIGS. 12-15, another multi-port therapy unit 600 is presented. The multi-port therapy unit 600 is analogous in most respects to the multi-port therapy unit 600 of FIGS. 9-11, and accordingly, some parts are labeled but not further described here. A main difference between the multi-port therapy unit 600 of FIGS. 12-15 and the multi-port therapy unit 600 of FIGS. 9-11 is that the plurality of canisters has been moved to the front face 610. In FIG. 12, an illustrative multi-lumen reduced-pressure delivery conduit 620 is shown coupled to the port 607 associated with one canister 606.

Figure 16:
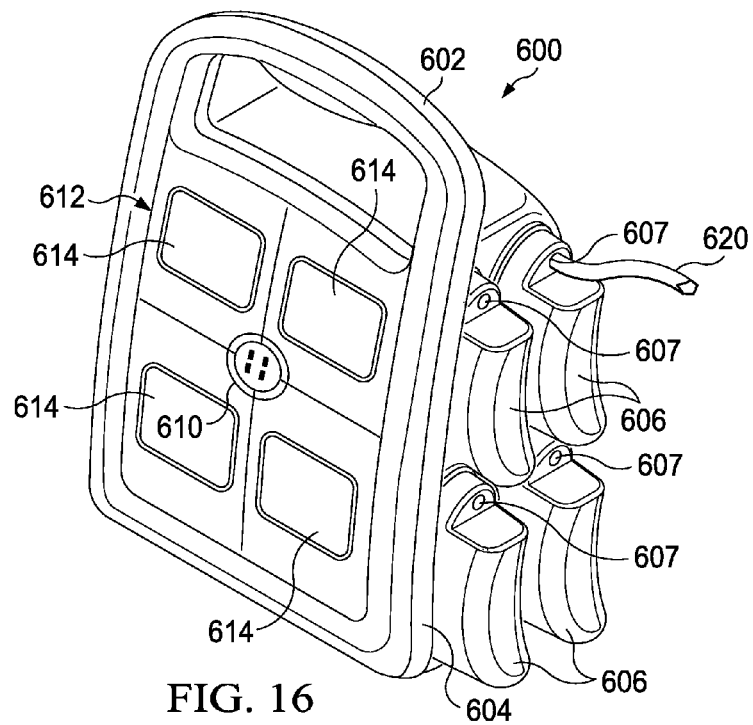
FIG. 16 is a perspective view of an illustrative embodiment of a multi-port therapy unit.
Figure 17:
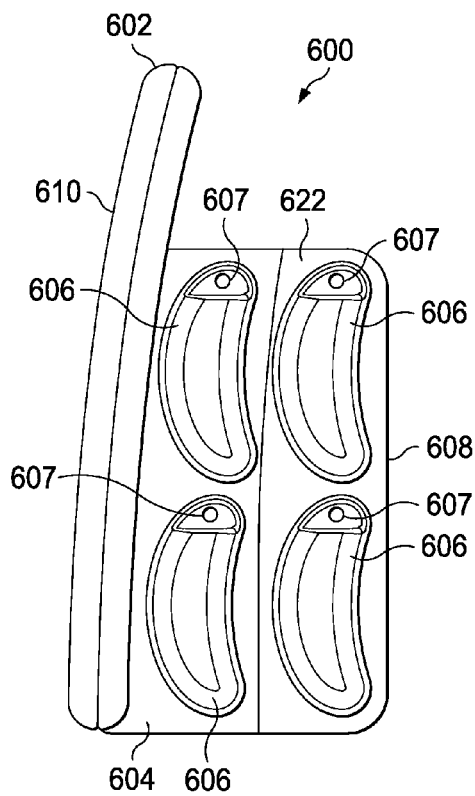
FIG. 17 is a side elevation view of the multi-port therapy unit of FIG. 16.
Figure 18:
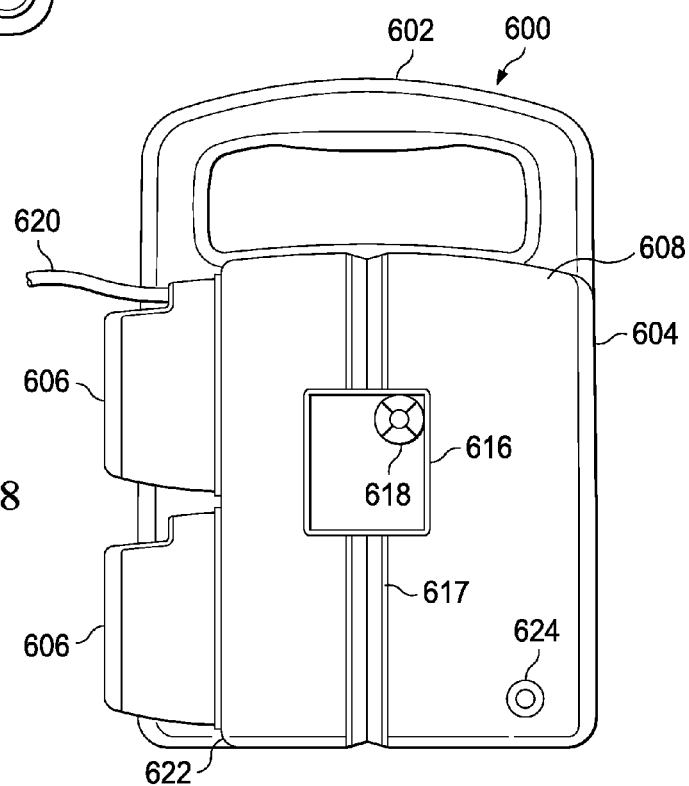
FIG. 18 is a rear elevation view of the illustrative multi-port therapy unit of FIG. 16.

Referring now primarily to FIGS. 16-18, another multi-port therapy unit 600 is presented. The multi-port therapy unit 600 is analogous in most respects to the multi-port therapy unit 600 of FIGS. 9-11, and accordingly, some parts are labeled but not further described here. A main difference between the multi-port therapy unit 600 of FIGS. 16-18 and the multi-port therapy unit 600 of FIGS. 9-11 is that the canisters 606 are coupled to the body 604 on a first side 622. For illustration purposes, one multi-lumen reduced-pressure delivery conduit 620 is shown coupled to a port 607 of one canister 606. Also shown is a power cord connection 624.

Figure 19:
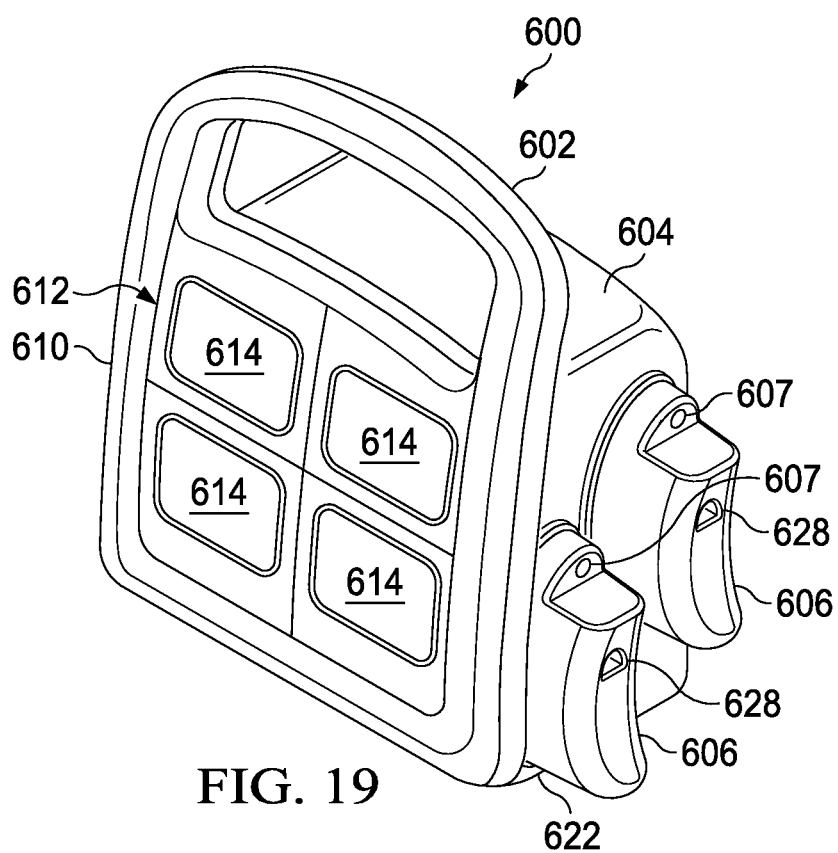
FIG. 19 is a perspective view of an illustrative embodiment of a multi-port therapy unit.
Figure 20:
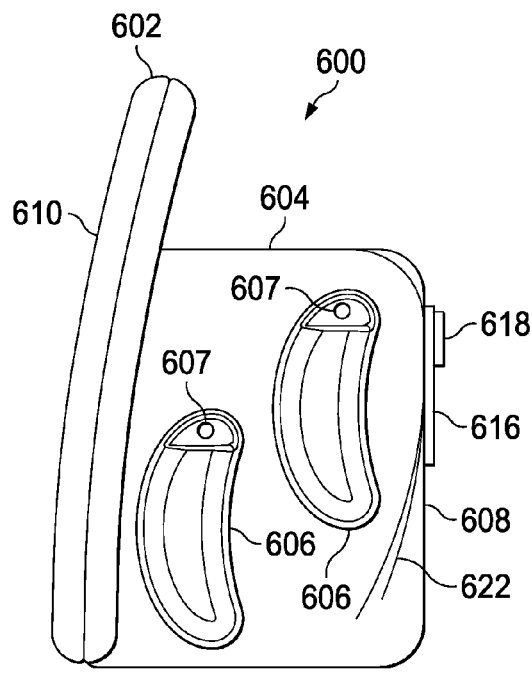
FIG. 20 is a side elevation view of the multi-port therapy unit of FIG. 19.
Figure 21:
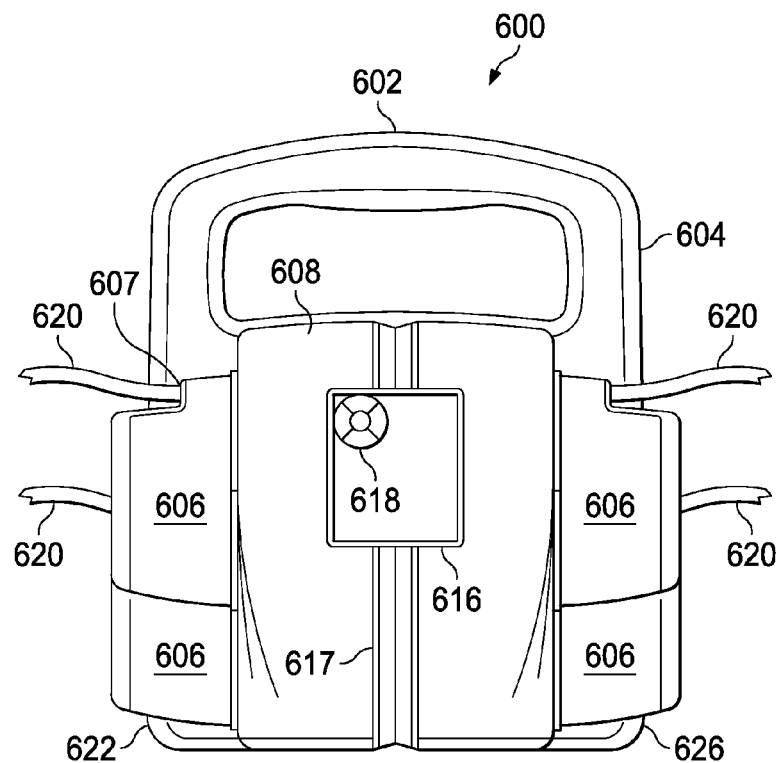
FIG. 21 is a rear elevation view of the multi-port therapy unit of FIG. 19.

Referring now primarily to FIGS. 19-21, another multi-port therapy unit 600 is presented. The multi-port therapy unit 600 is analogous in most respects to the multi-port therapy unit 600 of FIGS. 9-11, and accordingly, some parts are labeled but not further described here. A main difference between the multi-port therapy unit 600 of FIGS. 19-21 and the multi-port therapy unit 600 of FIGS. 9-11 is that the canisters 606 are coupled on a first side 622 and a second side 626. In addition, the canisters 606 on each side 622, 626 are staggered vertically (for orientation shown). The canisters 606 have a kidney shape that may be oriented differently on each side 622, 626. FIG. 21 shows four multi-lumen reduced-pressure delivery conduits 620 coupled to the multi-port therapy unit 600. A canister channel 628 to receive an attachment prong is shown in FIG. 19.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, aspects of any of the embodiments described above may be combined with aspects of any of the other embodiments described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A system for simultaneously treating a plurality of tissue sites, the system comprising:
   a plurality of reduced-pressure dressings;
   a plurality of multi-lumen reduced-pressure delivery conduits, wherein each multi-lumen reduced-pressure delivery conduit includes at least one pressure-sampling lumen and at least one reduced-pressure supply lumen, each multi-lumen reduced-pressure delivery conduit fluidly coupled to a respective reduced-pressure dressing of the plurality of reduced-pressure dressings;
   a multi-port therapy unit comprising:
      a body having at least two sides and an interior space,
      a plurality of patient-side ports on at least one side of the body, wherein each of the plurality of patient-side ports is configured to fluidly couple with at least one of the pressure-sampling lumens and one of the reduced-pressure supply lumens,
      a fluid reservoir completely disposed in the interior space of the body and fluidly coupled to each of the plurality of patient-side ports,
      a plurality of pressure sensors disposed in the interior space of the body and configured to determine a pressure associated with the pressure-sampling lumens of the respective multi-lumen reduced-pressure delivery conduit,
      a controller operatively coupled to the plurality of pressure sensors for receiving treatment pressure data from the plurality of pressure sensors, wherein the controller comprises a microprocessor and a memory configured to monitor pressure for each pressure sensor of the plurality of pressure sensors and to signal an alarm condition if the pressure is outside of a pre-selected range,
      a supply-side port for receiving reduced pressure, and
      an alarm indicator operatively coupled to the controller for indicating when the controller signals an alarm condition; and
   a reduced-pressure source fluidly coupled to the supply-side port of the multi-port therapy unit.

2. The system of claim 1, wherein the multi-port therapy unit further comprises:
   a drain conduit fluidly coupling the fluid reservoir with an exterior of the multi-port therapy unit for draining the fluid reservoir; and
   a valve associated with the drain conduit for selectively allowing fluid flow in the drain conduit.

3. The system of claim 1, wherein the multi-port therapy unit further comprises a plurality of visual indicators disposed on the multi-port therapy unit for providing a visual alert when a pressure below a first reduced-pressure threshold exists in at least one of the plurality of patient-side ports.

4. The system of claim 1, wherein the reduced-pressure source is a mobile therapy unit.

5. The system of claim 1, wherein the reduced-pressure source is wall suction.

6. The system of claim 1, wherein at least one of the plurality of pressure sensors is located proximate to a respective patient-side port and is configured to determine a pressure associated with the respective patient-side port.

7. The system of claim 1, wherein the alarm indicator comprises a plurality of alarm indicators disposed on at least one side of the body of the multi-port therapy unit, and each alarm indicator of the plurality of alarm indicators provides an indication of a pressure status of a respective patient-side port of the plurality of patient-side ports.

8. The system of claim 1, wherein each of the plurality of patient-side ports is configured to be coded with a unique identification of a respective reduced-pressure dressing of the plurality of reduced-pressure dressings.

9. The system of claim 1, wherein the multi-port therapy unit is a collapsible unit.

10. The system of claim 1, wherein each reduced-pressure dressing is discrete and configured to form a sealed space.

\* \* \* \* \*